(12) United States Patent
Wheeler

(10) Patent No.: US 6,696,424 B1
(45) Date of Patent: Feb. 24, 2004

(54) CYTOFECTIN DIMERS AND METHODS OF USE THEREOF

(75) Inventor: Carl Wheeler, Poway, CA (US)

(73) Assignee: Vical Incorporated, San Diego, CA (US)

( * ) Notice: Subject to any disclaimer, the term of this patent is extended or adjusted under 35 U.S.C. 154(b) by 0 days.

(21) Appl. No.: 09/580,463

(22) Filed: May 26, 2000

Related U.S. Application Data
(60) Provisional application No. 60/136,472, filed on May 28, 1999.

(51) Int. Cl.$^7$ ................................................ A01N 61/00
(52) U.S. Cl. ......................... 514/44; 424/450; 564/152; 564/157; 564/160
(58) Field of Search ........................... 424/450; 514/44; 564/157, 152, 160

(56) References Cited

U.S. PATENT DOCUMENTS

| | | | |
|---|---|---|---|
| 2,368,208 A | 1/1945 | Epstein et al. | 554/106 |
| 3,265,719 A | 8/1966 | Cowen et al. | 554/110 |
| 3,983,079 A | * 9/1976 | Spadini et al. | 510/237 |
| 4,713,339 A | 12/1987 | Levinson et al. | 435/240.2 |
| 4,864,060 A | 9/1989 | Karalis et al. | 564/292 |
| 4,897,355 A | 1/1990 | Eppstein et al. | 435/240.2 |
| 4,965,196 A | 10/1990 | Levinson et al. | 435/691 |
| 5,049,386 A | 9/1991 | Epstein et al. | 424/427 |
| 5,068,431 A | 11/1991 | Karalis et al. | 564/301 |
| 5,144,060 A | 9/1992 | Morita et al. | 560/170 |
| 5,264,618 A | 11/1993 | Felgner et al. | 560/224 |
| 5,279,833 A | 1/1994 | Rose | 424/450 |
| 5,334,761 A | 8/1994 | Gebeyehu et al. | 564/197 |
| 5,459,127 A | 10/1995 | Felgner et al. | 514/7 |
| 5,580,859 A | 12/1996 | Felgner et al. | 514/44 |
| 5,589,466 A | 12/1996 | Felgner et al. | 514/44 |
| 5,676,954 A | 10/1997 | Brigham | 424/450 |
| 5,693,622 A | 12/1997 | Wolff et al. | 514/44 |
| 5,703,055 A | 12/1997 | Felgner et al. | 514/44 |
| 5,861,397 A | 1/1999 | Wheeler | 514/247 |
| 6,034,271 A | 3/2000 | Kwetkat | 562/565 |

FOREIGN PATENT DOCUMENTS

| | | |
|---|---|---|
| JP | 61-130298 | 6/1986 |
| WO | WO 94/29469 | 12/1994 |
| WO | WO 97/11935 | 4/1997 |
| WO | WO 97/19675 | 6/1997 |
| WO | WO 97/31890 | 9/1997 |
| WO | WO 00/27795 | 5/2000 |

OTHER PUBLICATIONS

Hirata, H., et al., "Small–Angle Neutron–Scattering Study of Bis(quarternary ammonium bromide) Surfactant Micelles in Water. Effect of the Spacer Chain Length on Micellar Structure," *J. Phys Chem.* 99:17778–17784, American Chemical Society (1995).

McGregor, C., et al., "Rational Approaches to the Design of Cationic Gemini Surfactants for Gene Delivery," *J. Am. Chem. Soc.* 123:6215–6220, American Chemical Society (Jul. 2001; Published on Web Jun. 7, 2001).

Menger, F.M., and Keiper, J.S., "Gemini Surfactants," *Angew. Chem. Int. Ed.* 39:1906–1920, Wiley–VCH Verlag GmbH (Jun. 2000).

Menger, F.M., et al., "Gemini Surfactants with Acetylenic Spacers," *Langmuir* 16:2062–2067, American Chemical Society (2000; Published on Web Dec. 10, 1999).

Menger, F.M., and Littau, C.A., "Gemini Surfactants: A New Class of Self–Assembling Molecules," *J. Am. Chem. Soc.* 115:10083–10090, American Chemical Society (1993).

Menger, F.M., and Mbadugha, N.A., "Gemini Surfactants with a Disaccharide Spacer," *J. Am. Chem. Soc.* 123:875–885, American Chemical Society (Feb. 2001; Published on Web Jan. 16, 2001).

Peresypkin, A.V., and Menger, F.M., "Zwitterionic Geminis. Coacervate Formation from a Single Organic Compound," *Org. Lett.* 1:1347–1350, American Chemical Society (1999; Published on Web Oct. 2, 1999).

Pestman, J.M., et al., "Nonionic Bolaamphiphiles and Gemini Surfactants Based on Carbohydrates," *Langmuir* 13:6857–6860, American Chemical Society (1997).

Renout, P., et al., "Dimeric Surfactants: First Synthesis of an Asymmetrical Gemini Compound," *Tetrahedron Lett.* 39:1357–1360, Elsevier (1998).

van Doren, H.A., et al., "Mesogenic sugars. From aldoses to liquid crystals and surfactants," *Chem. Soc. Rev.* 29:183–199, Royal Society of Chemistry (May 2000).

Zana, R., "Gemini (dimeric) surfactants," *Curr. Opin. Colloid Interface Sci.* 1:566–571, Current Chemistry Ltd. (1996).

Kwetak, K., "Gemini–type betaine surfactants from amines and aldehydes," *Chem. Abstracts* 127:805, Abstract No. 127:249754r, The American Chemical Society (1997).

(List continued on next page.)

*Primary Examiner*—Dave T. Nguyen
*Assistant Examiner*—Richard Schnizer
(74) *Attorney, Agent, or Firm*—Sterne, Kessler, Goldstein & Fox P.L.L.C.

(57) ABSTRACT

A composition is provided comprising a novel cationic lipid compound having hydrophobic tails and two quaternary ammonium headgroups bridged by a linker. The composition is useful as a cytofectin for facilitating delivery and transfection of biologically active agents, particularly anionic bioactive agents such as DNA, into cells. The composition is useful also as an adjuvant for enhancing the humoral immune response of a vertebrate to an immunogen, especially an immunogen encoded by a polynucleotide-based vaccine. In certain preferred embodiments, the cationic lipid compound is a dimer containing quaternary ammonium headgroups bridged by a linker having DNA and/or cell receptor binding affinity, such as a polypeptide or polyamine. Also disclosed is an immunogenic composition comprising an immunogen and the composition of the present invention.

51 Claims, 4 Drawing Sheets

OTHER PUBLICATIONS

Dialog File 347, Accession No. 01916198, JAPIO English language abstract for JP 61–130298 (Document AP1). Jun. 18, 1986.

Bhattacharya, S., et al., "Synthesis and vesicle formation from novel pseudoglyceryl dimeric lipids. Evidence of formation of widely different membrane organizations with exceptional thermotropic properties," *Chem. Commun.* (23):2287–2288 (1997, Royal Society of Chemistry).

International Search Report for International Application No. PCT/US00/14676, mailed Sep. 29, 2000.

Barnfield, C., et al., "The Cellular Basis of Immune Induction at Mucosal Surfaces by DNA Vaccination," in *Development and Clinical Progress of DNA Vaccines, Dev. Biol. Stand.*, Brown, F., et al., eds., Basel Karger 104:159–164 (2000).

Felgner, J.H., et al., "Enhanced Gene Delivery and Mechanism Studies with a Novel Series of Cationic Lipid Formations," *J. Biol. Chem.* 269:2550–2561 (1994).

Menger, F.M., and Littau, C.A., "Gemini Surfactants: A New Class of Self–Assembling Molecules," *J. Am. Chem. Soc.* 115:1003–10090 (1993).

Nabel, G.J., et al., "Immunotherapy of Malignancy by In Vivo Gene Transfer into Tumors," *Hum. Gene Ther.* 3:399–410 (1992).

Norman, J., et al., "Adjuvants for Plasmid DNA Vaccines," in *Methods Mol. Med. Vol. 29, DNA Vaccines: Methods and Protocols*, Lowrie, D.B. and Whalen, R.G., Humana Press Inc., Totowa, N.J., pp. 185–196 (1998).

Rosenthal, A.F., and Geyer, R.P., "A Synthetic Inhibitor of Venom Lecithinase A," *J. Biol. Chem.* 235:2202–2206 (1960).

Solodin, I., and Heath, T.D., "Synthesis of Novel Cationic Lipids with a Guanidine Group, Cationic Lipids 3," *SYNLETT* (7):617–618 (1996).

Solodin, I., and Heath, T.D., "Synthesis of Amphiphilic Piperidinium Derivatives. Cationic Lipids 4," *SYNLETT* (7):619 (1996).

Solodin, I., and Heath, T.D., "Synthesis of Amphiphilic Derivatives of N–Methyldiethanolamine. Cationic Lipids 5," *SYNLETT* (7):620 (1996).

Agadjanyan, N.G., et al., "An HIV type 2 DNA Vaccine Induces Cross–Reactive Immune Responses against HIV type 2 and SIV," *AIDS Res. Hum. Retroviruses* 13(18):1561–1572 (Dec. 1997).

Agadjanyan, M.G., et al., "DNA Plasmid Based Vaccination Against the Oncogenic Human T Cell Leukemia Virus Type 1," *Curr. Top. Microbiol. Immunol.* 226:175–192 (1998).

Altman–Hamamdzic, S., et al., "Expression of β–galactosidase in mouse brain: utilization of a novel nonreplicative Sindbis virus vector as a neuronal gene delivery system," *Gene Ther.* 4(8):815–822 (Aug. 1997).

Bangham, et al., "Diffusion of Univalent Ions across the Lamellae," *J. Mol. Biol.* 23:238–252 (1965).

Behr, J.P., et al., "Efficient gene transfer into mammalian primary endocrine cells with lipopolyamine–coated DNA," *Proc. Natl. Acad. Sci. U. S. A.* 86(18):6982–6986 (Sep. 1989).

Boyer, J.D., et al., "In vivo protective anti–HIV immune responses in non–human primates through DNA immunization," *J. Med. Primatol.* 25(3):242–250 (Jun. 1996).

Boyer, J.D. et al., "DNA Vaccination as Anti–Human Immunodeficiency Virus Immunotherapy in Infected Chimpanzees," *J. Infect. Dis.* 176(6):1501–1509 (Dec. 1997).

Boyer, J.D., et al., "Protection of chimpanzees from high–dose heterologous HIV–1 challenge by DNA vaccination," *Nature Med.* 3(5):526–532 (May 1997).

Davis, H.L., "Plasmid DNA expression system for the purpose of immunization," *Curr. Opin. Biotechnol.* 8(5):635–646 (Oct. 1997).

Davis, H.L., et al., "DNA–based immunization against hepatitis B surface antigen (HBsAG) in normal and HBsAg–transgenic mice," *Vaccine* 15849–852 (Jun. 1997).

Davis, H.L., et al., "Direct gene transfer in skeletal muscle: plasmid DNA–based immunization against the hepatitis B virus surface antigen," *Vaccine* 12(16):1503–1509 (Dec. 1994).

Davis, H.L., et al., "Immune–mediated destruction of transfected muscle fibers after direct gene transfer with antigen–expressing plasmid DNA," *Gene Ther.* 4(3):181–188 (Mar. 1997).

DeBruyne, L.A. et al., "Lipid–mediated gene transfer of viral IL–10 prolongs vascularized cardiac allograft survival by inhibiting donor–specific cellular and humoral immune responses," *Gene Ther.* 5(8):1079–1087 (Aug. 1998).

Duzgunes, N., "Membrane fusion," in *Subcellar Biochemistry*, Roodyn, D.B., ed., Plenum Press, New York, vol. 11, pp. 195–286 (1985).

Etchart, N., et al., "Class I–restricted CTL induction by mucosal immunization with naked DNA encoding measles virus haemagglutinin," *J. Gen. Virol.* 78( Pt.7):1577–1580 (Jul. 1997).

Felgner, P.L., et al., "Lipofection: a highly efficient, lipid–mediated DNA–transfection procedure," *Proc. Natl. Acad. Sci. U S A,* 84(21):7413–7417 (Nov. 1987).

Felgner, J.H., "Separation and Quantitation of Cationic Liposome Components by High Performance Liquid Chromatography with Evaporative Light–Scattering Detection," *Pharm Res.* 14(9):1269–1271 (Sep. 1997).

Felgner, P.L., "Nonviral Strategies for Gene Therapy," *Sci. Am.* 276:102–106 (Jun. 1997).

Fukanaga, M., et al., "Liposome Entrapment Enhances the Hypocalcemic Action of Parenterally AdministeredC," *Endocrinology* 115(2):757–761 (Aug. 1984).

Gramzinski, R.M., et al., "Immune Response to a Hepatitis B DNA in Aotus Monkeys: A Comparison of Vaccine Formulation, Route, and Method of Administration," *Mol. Med.* 4(2):109–118 (Feb. 1998).

Gregoriadis, G., et al., "Liposome–mediated DNA vaccination," *FEBS Lett.* 402(2–3):107–110 (Feb. 1997).

Hartikka, J., et al., "An Improved Plasmid DNA Expression Vector for Direct Injection into Skeletal Muscle," *Human Gene Ther.* 7(10):1205–1217 (Jun. 1996).

Heppel, J., et al., "Development of DNA vaccines for fish: vector design, intramuscular injection and antigen expression using viral haemorrhagic septicaemia virus genes as model," *Fish and Shellfish Immunol.* :271–286 (1998).

Horn, et al., "Cancer Gene Therapy Using Plasmid DNA: Purification of DNA for Human Clinical Trials," *Human Gene Ther.* 6:656–573 (1995).

Ishif, N., et al., "Cationic LiposomesA a Strong Adjuvant for a DNA Vaccine of Human Immunodeficiency Virus Type 1," *AIDS Res. Hum. Retroviruses* 13(16):1421–1428 (Nov. 1997).

Kim, S., et al., "Preparation of Multivesicular Liposomes," *Biochim. Biophys. Acta* 728:339–348 (1983).

Klavniskis, L.S, et al., "Mucosal immunization with DNA–liposome complexes," *Vaccine* 15(8):818–820 (Jun. 1997).

Klavinskis, L.S., et al., "Intranasal Immunization with Plasmid DNA–Lipid Complexes Elicits Mucosal Immunity in the Female Genital and Rectal Tracts," *J. Immunol.* 162(1):254–262 (Jan. 1999).

Lodmell, D.L., et al., "Gene gun particle–mediated vaccination with plasmid DNA confers protective immunity against rabies virus infection," *Vaccine* 16:(2–3):115–118 (Jan.–Feb. 1998).

Lodmell, D.L., et al., "DNA Immunization protects nonhuman primates against rabies virus," *Nature Med.* 4(8):949–952 (Aug. 1998).

Mayer, L.D., et al., "Vesicles of variable sizes produced by a rapid extrusion procedure," *Biochim. Biophys. Acta* 858(1):161–168 (Jun. 1986).

Mayhew, E., et al., "Characterization of Liposomes Prepared Using a Microemulsifier," *Biochim. Biophys. Acta* 775(2):169–174 (Aug. 1984).

Nishizawa, et al., "Anion Recognition by Urea and Thiourea Groups: Remarkably Simple Neutral Receptors for Dihydroenphosphate," *Tetrahedron Lett.* 36(36):6483–6486 (1995).

Okada, E., et al., "Intranasal Immunization of a DNA Vaccine with IL–12– and Granulocyte–Macrophage Colony–Stimulating Factor (GM–CSF)–Expressing Plasmids in Liposomes Induces Strong Mucosal and Cell–Mediated Immune Responses Against HIV–1 Antigens," *J. Immunol.* 159(7):3638–3647 (Oct. 1997).

Olson, F., et al., "Preparation of Liposomes of Defined Size Distribution by Extrusion Through Polycarbonate Membranes," *Biochim. Biophys. Acta* 557(1):9–23 (Oct. 1979).

Qin, Y.J., et al., "Gene Suture—A Novel Method for Intramuscular Gene Transfer and its Application in Hypertension Therapy," *Life Sci.* 65(21):2193–2203 (1999).

Sambrook et al., in *Molecular Cloning, A Laboratory Manual,* 2nd ed., Cold Spring Harbor Laboratory Pres, p. A–2 (1989).

Sasaki, S., et al., "Monophosphoryl Lipid A Enhances Both Humoral and Cell–Mediated Immune Responses to DNA Vaccination Against Human Immunodeficiency Virus Type 1," *Infect. Immun.* 65(9):3520–3528 (Sep. 1997).

Sasaki, S., et al., "Adjuvant effect of Ubenimex on a DNA vaccine for HIV–1," *Clin. Exp. Immunol.* 111(1):30–35 (Jan. 1998).

Sasaki, S., et al., "Induction of Systemic and Mucosal Immune Responses to Human Immunodeficiency Virus Type 1 by a DNA Vaccine Formulated with QS–21 Saponin Adjuvant via Intramuscular and Intranasal Routes," *J. Virol.* 72(6):4931–9 (Jun. 1998).

Schrijver, R.S., et al., "Immunization of cattle with a BHV1 vector vaccine or a DNA vaccine both coding for the G protein BRSV," *Vaccine* 15(17–18) 1908–1916 (Dec. 1997).

Stephan, D.J., et al., "A New Cationic Liposome DNA Complex Enhances the Efficiency of Arterial Gene Transfer In Vivo," *Human Gene Ther.* 7(15):1803–1812 (Oct. 1996).

Strauss, J.K., et al., "DNA bending by hexamethylene–tethered ammonium ions," *Proc. Natl. Acad. Sci. U S A.* 93(18):9515–9520 (Sep. 1996).

Szoka, F., et al., "Procedure for preparation of liposomes with large internal aqueous space and high capture by reverse–phase evaporation," *Proc. Natl. Acad. Sci. U S A.* 75(9):4194–4198 (Sep. 1978).

Ulmer, J.B., et al., "Heterologous Protection Against Influenza by Injection of DNA Encoding a Viral Protein," *Science* 259:5102):1745–9 (Mar. 1993).

Ulmer, J.B., et al., "DNA Vaccines for Bacteria and Viruses," *Adv. Exp. Med. Biol.* 397:49–53 (1996).

Ulmer, J.B., et al., "DNA vaccines," *Curr. Opin. Immunol.* 8(4):531–536 (Aug. 1996).

Ulmer, J.B., et al., "Generation of MHC class I–restricted cytotoxic T Lymphocytes by expression of a viral protein in muscle cells: antigen presentation by non–muscle cells," *Immunology* 89(1):59–67 (Sep. 1996).

Ulmer, J .B., et al., "Toward the development of DNA vaccines," *Curr. Opin. Biotechnol.* 7(6):653–658 (Dec. 1996).

Vahising, H.L., et al.,Immunization with plasmid DNA using a pneumatic gun, *J. Immunol. Methods* 175(1):11–22 (Sep. 1994).

Vanderzanden, L., et al., "DNA Vaccines Expressing either the GP or NP Genes of Ebola Virus Protect Mice from Lethal Challenge," *Virology* 246(1):134–44 (Jun. 1998).

Wang, B., et al., "Mucosal immunization with a DNA vaccine induces immune responses against HIV–1 at a mucosal site," *Vaccine* 15(8):821–825 (Jun. 1997).

Wheeler, C.J., et al., "A novel cationic lipid greatly enhances plasmid DNA delivery and expression in mouse lung," *Proc. Natl. Acad. Sci. U S A.* 93(21):11456–11459 (Oct. 1996).

Wheeler, C.J., et al., "Converting an alcohol to an amine in a cationic lipid dramatically alters the co–lipid requirement, cellular transfection activity and the ultrastructure of DNA–cytofectin complexes," *Biochim. Biophys. Acta* 1280(1):1–11 (Apr. 1996).

Yokoyama, M., et al., "DNA immunization Effects of vehicles and route of administration on the induction of protective antiviral immunity," *FEBS Immunol. Med. Microbiol.* 14(4):221–230 (Jul. 1996).

* cited by examiner

CYTOFECTIN DIMERS AND METHODS OF USE THEREOF

CROSS-REFERENCE TO RELATED APPLICATIONS

This application claims priority under Section 119(e)(1) to U.S. Provisional Patent Application No. 60/136,472, filed May 28, 1999.

FIELD OF THE INVENTION

The present invention relates generally to cytofectin and adjuvant compositions. More particularly, the present invention provides compositions useful as cytofectins and as adjuvants, as well as methods for facilitating the transfection of nucleic acids into cells and for enhancing the humoral immune response of vertebrates to polynucleotide-based vaccines.

BACKGROUND OF THE INVENTION

Cytofectins are used to enhance the delivery of biologically active agents, particularly polynucleotides, proteins, peptides, and drug molecules, by facilitating transmembrane transport or by encouraging adhesion to biological surfaces. Some bioactive substances do not need to enter cells to exert their biological effect, because they operate either by acting on cell surfaces through cell surface receptors or to cell surfaces by interacting with extracellular components. However, many natural biological molecules and their analogues, including proteins and polynucleotides, or foreign substances, such as drugs, which are capable of influencing cell function at the subcellular or molecular level are preferably incorporated within the cell in order to produce their effect. For these agents, the cell membrane presents an impermeable selective barrier.

Successful intracellular delivery of agents not naturally taken up by cells has been achieved by exploiting the natural process of intracellular membrane fusion, or by direct access of the cell's natural transport mechanisms, which include endocytosis and pinocytosis (Duzgunes, N., *Subcellular Biochemistry* 11:195-286 (1985)). In addition, the cell membrane barrier can be overcome by complexing the agent to be delivered or transfected with lipid formulations closely resembling the lipid composition of natural cell membranes. These lipids are able to fuse with the cell membranes on contact, and in the process, the agents associated with the lipid complexes or aggregates are delivered intracellularly. Lipid aggregates comprising charged lipids can not only facilitate intracellular transfers by fusing with cell membranes but also by overcoming charge repulsions between the cell membrane and the agent to be delivered.

Cellular delivery of beneficial or interesting proteins can be achieved by introducing expressible DNA or mRNA into cells, a technique known as transfection. Nucleotide sequences introduced in this way can produce the corresponding protein encoded by the nucleotide sequence. The therapy of many diseases could be enhanced by the induced intracellular production of peptides which could remain inside the target cell, be secreted into the local environment of the target cell, or be secreted into the systemic circulation to produce their effect. Various techniques for introducing the DNA or mRNA precursors of bioactive peptides into cells include the use of viral vectors, including recombinant vectors and retroviruses, which have the inherent ability to penetrate cell membranes. However, the use of such viral agents to integrate exogenous DNA into the chromosomal material of the cell carries a risk of damage to the genome and the possibility of inducing malignant transformation. Another aspect of this approach which restricts its use in vivo is that the integration of DNA into the genome accomplished by these methods implies a loss of control over the expression of the peptide it codes for, so that transitory therapy is difficult to achieve and potential unwanted side effects of the treatment could be difficult or impossible to reverse or halt.

A major advance in the area of DNA transfection was the discovery that certain synthetic cationic lipids, such as DOTMA, in the form of liposomes or small vesicles, could interact spontaneously with DNA to form lipid-DNA complexes that are capable of fusing with the negatively charged lipids of the cell membranes, resulting in both uptake and expression of the DNA (see, e.g., Feigner, P. L. et al., *Proc Natl Acad Sci USA* 84:7413-7417 (1987) and U.S. Pat. No. 4,897,355, the disclosures of which are incorporated herein by reference). The well-known Lipofectin™ reagent (Bethesda Research Laboratories, Gaithersburg, Md.), an effective agent for the delivery of highly anionic polynucleotides into living tissue culture cells, comprises positively charged DOTMA liposomes which interact spontaneously with negatively charged polynucleotides to form complexes. In part, the effectiveness of cationic lipids as cytofectins is thought to result from their enhanced affinity for cells, many of which bear regions of high negative charge on their membrane surfaces. Also in part, the presence of positive charges on a lipid aggregate comprising a cationic lipid enables the aggregate to bind polyanions, especially nucleic acids. Lipid aggregates prepared in this way can spontaneously attach to negative charges on cell surfaces, can fuse with the plasma membrane, and can efficiently deliver functional polynucleotides into cells. More recently, other cationic lipids, including diesters and diethers of modified Rosenthal Inhibitor (RI) compounds, have been found to be effective cytofectin compounds (see, e.g., U.S. Pat. Nos. 5,459,127 and 5,264,618, the disclosures of which are incorporated herein by reference).

In the late 1980s, it was discovered that direct intramuscular (i.m.) injection of lipid-DNA complexes results in measurable protein expression, and also that "naked" plasmid DNA (pDNA) can be taken up and expressed in muscle to a greater extent than lipid-DNA complexes (Felgner, 1997)). One of the first applications of pDNA injection technology was the induction of an immune response. In 1991, it was first reported that mice could be immunized against HIV gp120 by i.m. vaccination with gp120 plasmid DNA (Felgner et al., 1991), and that mice could be protected from a lethal challenge of influenza virus after DNA immunization with influenza nucleoprotein (NP) antigen. Protection obtained after immunization with the highly conserved NP antigen extended across two different viral strains (Ulmer et al., 1996)). Numerous publications in the field of polynucleotide-based vaccination followed thereafter (Boyer et al., 1996; Boyer et al., 1997; Davis et al., 1997; Wang et al., 1997; Agadjanyan et al., 1998; Heppell et al., 1998; Lodmell et al., 1998; Vanderzanden et al., 1998)).

A problem often encountered in the course of polynucleotide-based vaccination is insufficient or suboptimal humoral response. To obtain a stronger humoral and/or cellular response, it is common to administer such vaccines in an immunogenic composition containing an adjuvant, a material which enhances the immune response of the patient to the vaccine. Adjuvants are useful generally for improving the immune response of an organism to a particular immunogen and are commonly included in vaccine compositions to increase the amount of antibodies produced and/or to reduce the quantity of immunogen and the frequency of administration.

A variety of adjuvants have been reported to effect differing levels of immune response enhancement to polynucleotide-based vaccination. Examples of such adjuvant materials include semi-synthetic bacterial cell wall-derived mono-phosphoryl lipid A (Sasaki, S. et al., *Infection and Immunity* 65(9):3250–3258 (1997)), small molecule immunostimulators (Sasaki, S. et al., *Clin Exp Immunol* 111:30–35 (1998)), and saponins (Sasaki, S. et al., *J Virol* 72(6):4391–4939 (1998)). The immune response from i.m. pDNA vaccination has also been enhanced through the use of cationic lipids (e.g., Ishii, N. et al., *Aids Res Hum Retroviruses* 13(16):1421–1428 (1997)), Okada, E. et al., *J Immunology* 159:3638–3647 (1997); Yokoyama, M. et al., *FEMS Immunol Med Microbiol* 14:221–230 (1996); Gregoriadis, G. et al., *FEBS Letters* 402:107–110 (1997); Gramzinski, R. A. et al., *Molecular Medicine* 4:109–118 (1998); Klavinskis, L. S. et al., *Vaccine* 15(8):818–820 (1997); Klavinskis, L. S. et al., *J Immunology* 162:254–262 (1999); Etchart, N. et al, *J Gen Virology* 78:1577–1580 (1997); Norman, J. et al., in *Methods in Molecular Medicine, Vol. 9; DNA Vaccines: Methods and Protocols*, D. B. Lowrie and R. Whalen, eds., Chapter 16, pp. 1–13 (1999)). Cationic lipids were originally studied as cytofectins to enhance the transfection and delivery of pDNA into cells in vitro (see, e.g., cytofectins disclosed and claimed in U.S. Pat. Nos. 5,334,761, 5,459,127 and 5,264,618, the disclosures of which are incorporated herein by reference); however, further development has led to successful specific applications of protein delivery in vivo (Wheeler, C. J. et al., *Proc Natl Acad Sci USA* 93:11454–11459 (1996); Stephan, D. J. et al, *Human Gene Therapy* 7:1803–1812 (1996); DeBruyne, L. A. et al., *Gene Therapy* 5:1079–1087 (1998)).

SUMMARY OF THE INVENTION

The present invention is directed in certain embodiments to cytofectin and adjuvant compositions, as well as to immunogenic compositions comprising immunogens and such adjuvant compositions. In other embodiments, the present invention relates to methods for facilitating the transfection and delivery of bioactive agents into cells, and to methods for enhancing the humoral immune responses of vertebrates to polynucleotide-based vaccines.

The present invention also provides methods for facilitating transfection and delivery of bioactive agents into cells, as well as methods for enhancing the immune response of vertebrates to immunization, particularly pDNA immunization. The present invention is especially useful in this latter regard by providing enhanced humoral immune response, as evidenced by the level of antibody titers, to polynucleotide-based vaccines. Elevation of antibody levels is particularly advantageous in applications where antibody levels from the immunogen-encoding nucleotide sequence alone are sub-optimal. In a related advantage, if the desired level of antibodies is produced with a given dose of pDNA, the amount of pDNA necessary to reach the predetermined antibody titer level can be reached using a lower pDNA dose. For pDNA vaccination applications, this advantage is important because acceptable vaccination volumes, coupled with functional limits on the concentration of pDNA, define an upper limit on a given vaccine dose. This advantage is particularly important for vaccines containing multiple plasmids, each of which must be present in sufficient quantity to elicit an immune response to its particular transgene.

With regard to the polynucleotide-based vaccination aspect, the methods of the present invention are useful prophylactically to protect a vertebrate from a disease, therapeutically to treat a diseased vertebrate, or both. In certain preferred embodiments, the present invention is directed to a method for immunizing a vertebrate by administering to the vertebrate an immunogenic composition which includes a nucleotide sequence that encodes an immunogen, and an adjuvant composition comprising a novel cationic lipid compound having two quaternary ammonium headgroups bridged by a linker. The immunogen-encoding nucleotide sequence, upon incorporation into the cells of the vertebrate, produces an immunologically effective amount of an immunogen (e.g., an immunogenic protein). The adjuvant composition of the present invention enhances the immune response of the vertebrate to the immunogen.

In certain embodiments, the compositions of the present invention further include one or more co-lipids or other lipid aggregate-forming components such as, for example, phospholipids, lysophospholipids, lysolipids and cholesterol. Such co-lipids include cationic, anionic and neutral lipids. Other appropriate co-lipids for use in the present invention are known to or may be determined by those skilled in the art.

One aspect of the present invention is a composition comprising a novel cationic lipid compound having hydrophobic tails and two quaternary ammonium headgroups bridged by a linker, the cationic lipid compound having a structure according to general formula (I) or (II) described below.

In certain preferred embodiments, where the cationic lipid compound has a structure according to formula (I), the linker is optionally substituted $C_1$ to $C_{10}$ alkyl or alkyloxy, or optionally substituted $C_1$ to $C_{10}$ alkenyl or alkenyloxy. In a particularly preferred embodiment, the cationic lipid compound is PentaEG-bis-DMRIE, the chemical structure of which is shown in FIG. 1B. The chemical name of PentaEG-bis-DMRIE is penta(ethylene glycol), α, ω-bis-(±)-N-hydroxyethyl)-N,N-dimethyl-2,3-bis(tetradecyloxy)-1-propanaminium bromide ether.

In certain other embodiments, the linker preferably includes a ureyl linkage (i.e., —NR—C(O)—NR—, where R is H or optionally substituted $C_1$ to $C_{10}$ alkyl or alkenyl), a bis-ureyl linkage (i.e., —NR—C(O)—NR—R'—NR—C(O)—NR—, where R is H or optionally substituted $C_1$ to $C_{10}$ alkyl or alkenyl, and R' is optionally substituted $C_1$ to $C_{10}$ alkyl or alkenyl), or a peptide linkage (i.e., —C(O)—NR—, where R is H or optionally substituted $C_1$ to $C_{10}$ alkyl or alkenyl). These compositions may further include one or more co-lipids.

In certain other preferred embodiments, where the cationic lipid compound has a structure according to formula (I) described below, the linker has DNA and/or cell receptor binding affinity. Such linkers may enhance the effectiveness of the lipid in interacting with nucleotides and/or cell membranes. Examples of moieties having such binding affinity include, for example, amino acids, peptides, saccharides, polypeptides, polysaccharides, proteins, polyamines, peptidomimetic moieties and histories. Specific examples of polyamines having such binding affinity include spermine, spermidine, and derivatives thereof. In particularly preferred embodiments incorporating a peptide moiety, the cationic lipid is HB-DMRIE-Ox-Trp-γ-DMRIE or PEG34-bis-But-DMRIE-propylamide, the chemical structures of which are shown in FIG. 1B. The chemical name of HB-DMRIE-Ox-Trp-γ-DMRIE is (±)-N-[4-(N'-(3'-tryptophanylaminopropyl))-N',N'-dimethyl-2', 3'-bis(tetradecyloxy)-1'-propanaminiumyl]-N,N-dimethyl-2,3-bis(tetradecyloxy)-1-propanaminium bromide. The molecular formula of HB-DMRIE-Ox-Trp-γ-DMRIE is $C_{84}H_{161}Br_2N_5O_6$. The chemical name of PEG34-bis-But-DMRIE-propylamide is poly(ethylene glycol)-34 bis-[(±)-N-(N'-propylbutyramido)-N,N-dimethyl-2,3-bis(tetradecyloxy)-1-propanaminium bromide].

In yet other preferred embodiments, where the cationic lipid compound has a structure according to formula (II), the linker bridging the quaternary ammonium headgroups includes a bis-ureyl linkage. In certain embodiments, the cationic lipid compound is a dimer, wherein the hydrophobic lipid tails, represented by groups $R_1$ to $R_4$, are identical. In particularly preferred embodiments, the cationic lipid compound is SBDU-DMRIE, SBGU-DMREE or SHGU-DMRIE, the chemical structures of which are provided in FIG. 1A. Another common name of SBDU-DMRIE is butane bis-DU-DMRIE. The chemical name of SBDU-DMRIE is 1,4-bis-(N'-butyl-(4-(N,N-dimethyl-2,3-bis(tetradecyloxy)-1-propanaminium))-ureyl-butane. The molecular formula is $C_{80}H_{166}O_6N_6$. Another common name of SHGU-DMRIE is hexane bis-1,6-GU-DMRIE. The chemical name of SHGU-DMRIE is 1,4-bis-(N'-propyl-(4-(N,N-dimethyl-2,3-bis(tetradecyloxy)-1-propanaminium))-ureyl-hexane. The molecular formula is $C_{80}H_{166}O_6N_6$. Another common name of SBGU-DMRIE is butane bis-GU-DMRIE. The chemical name of SBGU-DMRIE is 1,4-bis-(N'-propyl-(4-(N,N-dimethyl-2,3-bis(tetradecyloxy)-1-propanaminium))-ureyl-butane. The molecular formula is $C_{80}H_{166}O_6N_6$. These compositions may also optionally include one or more co-lipids.

Another aspect of the present invention is an immunogenic composition comprising an immunogen and an adjuvant composition comprising a cationic lipid compound according to general formula (I) or (II) described below. Preferably, the immunogen is provided by an immunogen-encoding nucleotide sequence which, most preferably, is a plasmid DNA, or a portion thereof. The immunogenic composition may further include one or more co-lipids.

Still another aspect of the present invention is a method for inducing an immune response in a vertebrate by administering to the vertebrate an immunogenic composition, which includes one or more immunogen-encoding nucleotide sequences, and an adjuvant composition which includes one or more cationic lipid compounds according to general formula (I) or (II) described below, in an amount sufficient to generate an immune response to the encoded immunogen. The vertebrate is preferably a mammal and, most preferably, is a human.

Yet another aspect of the present invention is a method useful for delivering a biologically active agent to a cell of a plant or animal. The method involves preparing a lipid aggregate comprising the biologically active agent and a composition including one or more cationic lipid compounds according to general formula (I) or (II) described below, followed by contacting the cell with the lipid aggregate. This method is useful for both in vivo and in vitro delivery to cells, and may be utilized for the transfection of cells.

Yet another aspect of the present invention is a pharmaceutical preparation comprising a cytofectin/adjuvant composition including a cationic lipid compound according to general formula (I) or (II) together with a pharmacologically effective amount of a therapeutic agent. The cytofectin composition facilitates the cellular delivery of the therapeutic agent. Preferably, the therapeutic agent is a polynucleotide, such as an antisense RNA or DNA molecule. The polynucleotide can encode an immunogen, a natural hormone, or a synthetic analogue of a natural hormone, or it can encode a gene product that is deficient or absent in a disease state, and administration of the gene product to a vertebrate has a therapeutic effect.

BRIEF DESCRIPTION OF THE FIGURES

The foregoing aspects and advantages of the present invention will be readily apparent to one skilled in the art upon reference to the figures and the detailed description which follows.

DETAILED DESCRIPTION OF PREFERRED EMBODIMENTS OF THE INVENTION

Figure 1A:
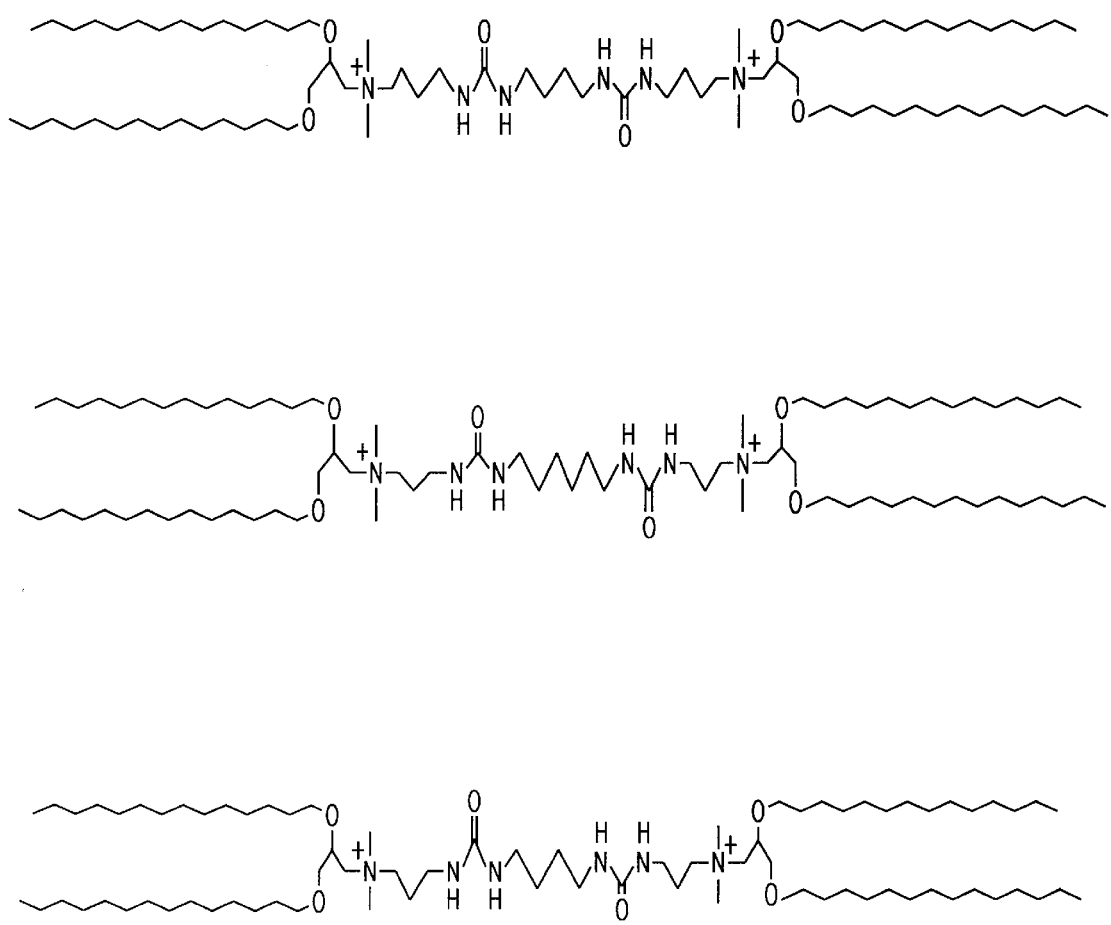
FIGS. 1A and, 1B provide the chemical structures for six preferred cationic lipid compounds for use in the compositions of the present inventions: SBDU-DMRIE; SBGU-DMRIE; HB-DMREE-Ox-Trp-γ-DMRIE; PentaEG-bis-DMRIE; and PEG34-bis-But-DMRIE-propylamide.

It will be apparent to one skilled in the art, in view of the following detailed description and the claims appended hereto, that various substitutions and modifications may be made to the present invention without departing from the scope of the invention as claimed.

The present invention provides compositions comprising a novel cationic lipid compound having hydrophobic alkyl tails and two quaternary ammonium headgroups bridged by a linker, the cationic lipid compound having a structure according to general formula (I) or (II) described below. These compositions may be used as cytofectins and/or adjuvants. As cytofectins the compositions facilitate the intracellular delivery of bioactive agents, such as, for example, nucleotide sequences, proteins, peptides and drugs, into the cells of plants and animals, both for in vivo and in vitro applications. As adjuvants the compositions enhance the humoral immune response of a vertebrate to an immunogen.

The cationic lipid compounds of the present invention include those having the general formula (I):

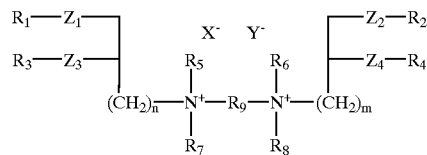

wherein $Z_1$, $Z_2$, $Z_3$ and $Z_4$ are the same or different and are —O—C(O)— or —O—;

$R_1$ and $R_2$ are the same or different and are H, $C_1$ to $C_{24}$ alkyl or $C_1$ to $C_{24}$ alkenyl;

$R_3$ and $R_4$ are the same or different and are $C_1$ to $C_{24}$ alkyl or $C_1$ to $C_{24}$ alkenyl;

$R_5$, $R_6$, $R_7$ and $R_8$ are the same or different and are H, $C_1$ to $C_{10}$ alkyl or $C_1$ to $C_{10}$ alkenyl;

$R_9$ is a linker;

n and m are the same or different and are 1 to 8; and

X and Y are the same or different and are non-toxic anions.

The cationic lipid compounds of the present invention are useful as cytofectins because they may be processed to form lipid aggregates together with bioactive agents. Quaternary ammonium groups are known to possess binding affinity to nucleic acids, making the cationic lipid compounds particularly useful for the cellular delivery of nucleotide sequences, such as found in pDNA vaccines. For a discussion of the binding affinity of bidentate quaternary diammonium ions with DNA, see, for example, Strauss et al., *Proc Natl Acad Sci USA* 93:9515–9520 (1996), which describes the interaction between DNA and hexamethylene-tethered ammonium ions.

Preferably, in certain embodiments, $R_9$ in formula (I) is a linker that possesses DNA and/or cell receptor binding affinity. Examples of such linkers include carbohydrates, polysaccharides, amino acids, peptides, polypeptides, proteins, antibodies, peptidomimetics, polyamines and histones. These types of linkers provide additional interactions with nucleotide sequences and/or with cell membranes, thereby increasing that cellular delivery potency of the cationic lipid compounds. This is particularly useful for the delivery of a bioactive agent to a selected target cell type, especially where the linker is able to bind specifically to a surface antigen or receptor on the membrane of the targeted cell. The ability to target a particular cell type is especially useful in in vivo applications (e.g., in gene therapy). Preferred linkers for this purpose include the polyamines spermine and spermidine (as well as derivatives thereof), and proteins rich in basic amino acids such as arginine and histidine (or derivatives or analogues thereof). Cationic substances such as the histones, spermines and spermidines are known to bind and modulate negatively-charged cell membrane surfaces. For example, lipid-derivatized spermine-like structures efficiently modulate gene transfer into mammalian endocrine cells (Behr, J-P. et al., *Proc Natl Acad Sci USA* 86:6982–6986 (1989)). Other preferred proteins useful as linkers include immunoglobulins (e.g., single chain immunoglobulins, immunoglobulin fragments), transferrin, asialoglycoproteins (e.g., asialofetuin), integrins, cytokines (e.g., interferons and interleukins), selectins, cell surface receptors, receptor ligands, major histocompatability proteins, lysosomotrophic proteins, extracellular proteins, proteins bearing internalization and/or nuclear localization signals, excreted proteins, protein hormones (e.g., insulin, erythropoetin), growth factors (e.g., human growth factor, insulin-like growth factor, epidermal growth factor), bacterial exotoxins, low density lipoprotein, alpha-2-macroglobulin, and angiotensin. In addition, fusion proteins and chimeric proteins comprising advantageous DNA binding and/or targeting properties alone or in combination are also contemplated as preferred linkers. The compositions in these embodiments may optionally include one or more co-lipids.

Figure 1B:
Figure 1B:
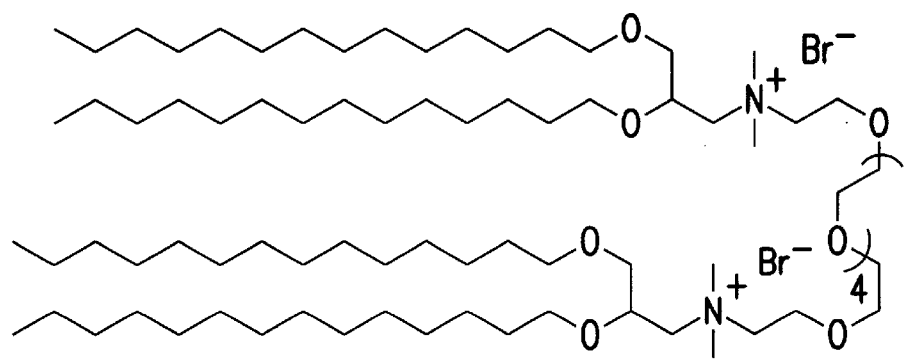
Figure 1B:
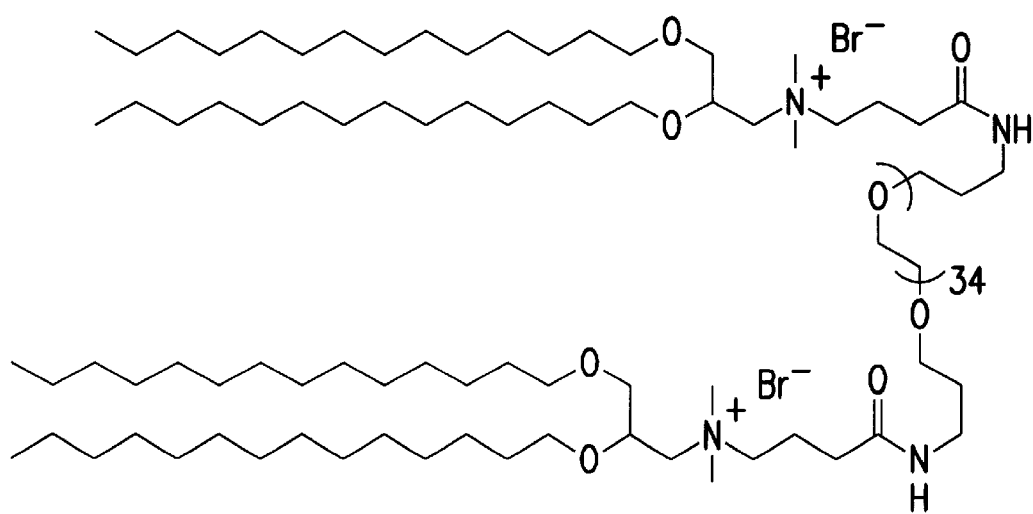

In certain preferred embodiments, where the cationic lipid compound is according to formula (I), the linker is optionally substituted $C_1$ to $C_{10}$ alkyl or alkyloxy, or optionally substituted $C_1$ to $C_{10}$ alkenyl or alkenyloxy. In a particularly preferred embodiment, the cationic lipid compound is PentaEG-bis-DMRIE, the chemical structure of which is shown in FIG. 1B.

In certain other embodiments, the linker preferably comprises a ureyl linkage (i.e., —NR—C(O)—NR—, where R is H or optionally substituted $C_1$ to $C_{10}$ alkyl or alkenyl), a bis-ureyl linkage (i.e., —NR—C(O)—NR—R'—NR—C(O)—NR—, where R is H or optionally substituted $C_1$ to $C_{10}$ alkyl or alkenyl, and R' is optionally substituted $C_1$ to $C_{10}$ alkyl or alkenyl), or a peptide linkage (i.e., —C(O)—NR—, where R is H or optionally substituted $C_1$ to $C_{10}$ alkyl or alkenyl). Such linkages provide the cationic lipids of the present invention additional binding affinity with anionic molecules such as DNA. In particularly preferred embodiments incorporating a peptide moiety, the cationic lipid compound is HB-DMRIE-Ox-Trp-γ-DMRIE or PEG34-bis-But-DMRIE-propylamide, the chemical structures of which are shown in FIG. 1B. The compositions in these embodiments may optionally include one or more co-lipids.

The cationic lipid compounds of the present invention also include those having the general formula (II):

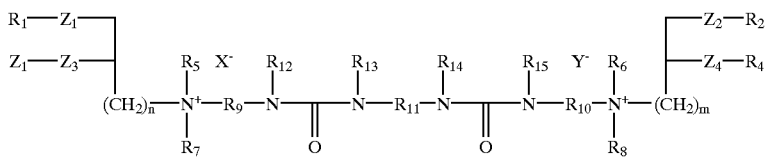

wherein $Z_1$, $Z_2$, $Z_3$ and $Z_4$ are the same or different and are —O—C(O)— or —O—;

$R_1$ and $R_2$ are the same or different and are H, $C_1$ to $C_{24}$ alkyl or $C_1$ to $C_{24}$ alkenyl;

$R_3$ and $R_4$ are the same or different and are $C_1$ to $C_{24}$ alkyl or $C_1$ to $C_{24}$ alkenyl;

$R_5$, $R_6$, $R_7$, $R_8$, $R_{12}$, $R_{13}$, $R_{14}$, and $R_{15}$ are the same or different and are H, $C_1$ to $C_{10}$ alkyl or $C_1$ to $C_{10}$ alkenyl;

$R_9$ and $R_{10}$ are the same or different and are optionally substituted $C_1$ to $C_{10}$ alkyl or $C_1$ to $C_{10}$ alkenyl;

$R_{11}$ is optionally substituted $C_1$ to $C_{10}$ alkyl or $C_1$ to $C_{10}$ alkenyl;

n and m are the same or different and are 1 to 8; and

X and Y are the same or different and are non-toxic anions.

In certain embodiments where the cationic lipid compound is according to formula (II) above, the linker bridging the quaternary ammonium headgroups includes a bis-ureyl linkage. Urea groups are recognized in the art for possessing binding affinity for phosphate groups, as found in cell membranes (see, e.g., Nishizawa et al., *Tetrahedron Lett.* 36(36):6483–6486 (1995)). In preferred embodiments, the cationic lipid compound is a dimer, wherein the hydrophobic lipid tails, represented by groups $R_1$ to $R_4$, are identical. In particularly preferred embodiments, the cationic lipid compound is SBDU-DMRIE, SBGU-DMRIE or SHGU-DMRIE, the chemical structures of which are provided in FIG. 1A. These compositions may also further include one or more co-lipids.

Various preferred cationic lipid compounds useful in the present invention include those based on or comprising the following structures: DMRIE ((±)-N-(2-hydroxyethyl)-N,N-dimethyl-2,3-(bis-tetradecyloxy)-1-propanaminium); DORIE ((±)-N,N-dimethyl-N-(2-hydroxyethyl)-2,3-(bis-syn-9-octadecenyloxy)-1-propanaminium); DLRIE ((±)-N-

(2-hydroxyethyl)-N,N-dimethyl-2,3-(bis-dodecyloxy)-1-propanaminium); DDRIE ((±)-N-(2-hydroxyethyl)-N,N-dimethyl-2,3-bis-decyloxy)-1-propanaminium); DPRIE ((±)-N-(2-hydroxyethyl)-N, N-dimethyl-2,3-(bis-hexadecyloxy)-1-propanaminium); and DMORIE ((±)-N-(2-hydroxyethyl)-N,N-dimethyl-2,3-(bis-syn-9-tetradeceneyloxy)-1-propanaminium).

For purposes of definition, the term "co-lipid" refers to any hydrophobic material which may be combined with a cationic lipid, and includes amphipathic lipids, such as phospholipids, and neutral lipids, such as cholesterol and other sterols, as well as lyso forms of such lipids. The co-lipids of the present invention can be any of the natural or synthetic phospholipids or mono-, di-, or triacylglycerols. The natural phospholipids are typically those from animal and plant sources, such as phosphatidylcholine, phosphatidylethanolamine, sphingomyelin, phosphatidylserine, or phosphatidylinositol. In one preferred embodiment, phosphatidylethanolamines include DOPE, DMPE, and DPyPE. DOPE and DPyPE are particularly preferred. As an adjuvant composition, the most preferred co-lipid is DPyPE, which comprises two phytanoyl substituents incorporated into the diacylphosphatidylethanolamine skeleton. Synthetic phospholipids typically are those having identical fatty acid groups, including, but not limited to, dimyristoylphosphatidylcholine, dioleoylphosphatidylcholine, dipalmitoylphosphatidylcholine, distearoylphosphatidylcholine and the corresponding synthetic phosphatidylethanolamines and phosphatidylglycerols. Neutral co-lipids include, for example, phosphatidylcholine, cardiolipin, phosphatidylethanolamine, mono-, di- or triacylglycerols, and analogues thereof. Examples of negatively charged lipids include phosphatidylglycerol, phosphatidic acid or a similar phospholipid analog. Other hydrophobic and amphiphilic "co-lipid" additives, such as, for example, sterols, fatty acids, gangliosides, glycolipids, lipopeptides, liposaccharides, neobees, niosomes, prostaglandins and sphingolipids, may also be used.

Preferably, the cationic lipid:co-lipid molar ratio in the cytofectin/adjuvant compositions of the present invention is from about 9:1 to about 1:9. More preferably, the cationic lipid:co-lipid molar ratio is from about 4:1 to about 1:4 and, still more preferably, is from about 2:1 to about 1:2. The most preferred molar ratio is about 1:1.

The cationic lipids of the present invention and (optionally) co-lipids may be mixed or combined in a number of ways to produce a variety of non-covalently bonded lipid aggregates. The term "lipid aggregate" includes, for example, liposomes, lipid vesicles (e.g., multilamellar vesicles and unilamellar vesicles), micelles, amorphous lipid complexes and aggregates, and simple films.

The compositions of the present invention can be prepared and used in a similar manner as prior art cytofectin or adjuvant compositions. Methods for preparing lipid aggregates, such as liposomes and lipid vesicles, are well known in the art. Representative methods are disclosed, for example, by Felgner et al., *Proc Natl Acad Sci USA* 84:7413–7417 (1987); Eppstein et al., U.S. Pat. No. 4,897,335; Bangham, A. et al., *J Mol Biol* 23:238–252 (1965); Olson, F. et al., *Biochim Biophys Acta* 557:9–23 (1979); Szoka, F. et al., *Proc Natl Acad Sci USA* 75:4194–4198 (1978); Mayhew, E. et al., *Biochim Biophys Acta* 775:169–175 (1984); Kim, S. et al., *Biochim Biophys Acta* 728:339–348 (1983); and Fukunaga, M. et al., *Endocrinol* 115:757–761 (1984), the disclosures of which are incorporated herein by reference. Commonly used techniques for preparing lipid aggregates of appropriate size for use as delivery vehicles include sonication and freeze-thaw plus extrusion. See, e.g., Mayer, L. et al., *Biochim Biophys Acta* 858:161–168 (1986).

In order to maximize homogeneity in the lipid aggregates, the cationic lipid and co-lipid (where included) components in the compositions of the present invention are preferably dissolved in a solvent such as chloroform, followed by evaporation of the solution under vacuum to dryness as a lipid film on the inner surface of a glass vessel (e.g., a Rotovap round-bottomed flask). Upon suspension in an aqueous solvent, the lipid molecules self-assemble into homogenous lipid vesicles. These lipid vesicles may subsequently be processed to have a selected mean diameter of uniform size prior to complexing with, for example, pDNA according to methods known to those skilled in the art. For example, the sonication of a lipid solution is described in Felgner et al., *Proc Natl Acad Sci USA* 84:7413–7417 (1987) and in U.S. Pat. No. 5,264,618, the disclosures of which are incorporated herein by reference.

The term "vertebrate" is intended to encompass a singular "vertebrate" as well as plural "vertebrates", and comprises mammalian and avian species, as well as fish.

The term "adjuvant" means any material having the ability to enhance the immune response to a particular immunogen. Such an ability is manifested by a significant increase in immune-mediated protection. Enhancement of humoral immune response is typically manifested by a significant increase in the titer of antibody raised to the immunogen.

The term "amino acid" refers to any naturally occurring or non-naturally occurring amino acid. This definition is intended to embrace substituted α-amino acids as well as non-α-amino acids. A non-α-amino acid is defined as an amino acid in which the amino group is attached to a carbon atom that is not adjacent to the carboxylic acid group.

The term "nucleotide sequence" refers to any one or more polynucleotides or polynucleotide segments or constructs (e.g., DNA or RNA oligomers, mRNA or pDNA). The nucleotide sequence may be provided in linear, circular (e.g., plasmid), or branched form as well as double-stranded or single-stranded form. The nucleotide sequences may comprise a conventional phosphodiester bond or a non-conventional bond (e.g., an amide bond, such as found in peptide nucleic acids (PNA)).

The term "alkyl" encompasses saturated (i.e., single bonded) straight-chain and branched-chain hydrocarbon moieties. The term "substituted alkyl" comprises alkyl groups further bearing one or more substituents selected from hydroxy, alkoxy (of a lower alkyl group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano; nitro, nitrone, oxy, amino, amido, imino, thio, —C(O)H, acyl, oxyacyl, carboxyl, carbamate, sulfonyl, sulfonamide, sulfuiryl, and the like.

The term "alkenyl" encompasses straight-chain and branched-chain hydrocarbon moieties having one or more double bonds. The term "substituted alkenyl" refers to alkenyl groups further bearing one or more substituents as set forth above.

The terms "alkyl" and "alkenyl" further encompass moieties which contain heteroatoms such as N, O, or S within the hydrocarbon backbone.

The term "peptide" refers to a molecule comprising two or more amino acids that are linked by means of peptide bonds. A "peptide bond" or "peptide linkage" is a covalent bond formed by splitting out a water molecule between the carboxyl group of one amino acid and the amino group of a second amino acid, and has the chemical structure —C(O)—NR—, where R is H, $C_1$ to $C_{10}$ alkyl or $C_1$ to $C_{10}$ alkenyl. This definition is intended to embrace any carboxylic acid and amino groups present in an amino acid molecule, as well as any carboxylic acid and amino groups in linked moieties which are not amino acids.

The term "polypeptide" refers to a polymer of more than ten amino acids that are linked by means of peptide bonds. The term "protein" refers to a high molecular weight polypeptide of amino acids, and includes, but is not limited to hormones, antibodies and certain antigens.

The term "polyamine" refers to an aliphatic compound comprising multiple amino and/or imino groups, such as spermine, spermidine, cadaverine and putrescine. The term "polyamine" includes polyamino acids.

The term "target cell" refers to any cell to which a desired agent is delivered, using the cytofectin compositions of the present invention.

The term "transfection" is used herein to mean the delivery of an expressible nucleotide sequence to a target cell, such that the target cell is rendered capable of expressing the nucleotide sequence. "Expression" means any manifestation of the functional presence of the nucleotide sequence in the cell, including, without limitation, both transient expression and stable expression. "Delivery" is used to denote a process by which a desired agent is transferred to a target cell such that the desired agent is ultimately located inside the target cell, or in or on the target cell membrane.

The present invention also provides an immunogenic composition comprising an immunogen and an adjuvant composition which includes a cationic lipid compound according to general formula (I) or (II). An "immunogen" is meant to encompass any antigenic or immunogenic polypeptides including poly-aminoacid materials having epitopes or combinations of epitopes, and immunogen-encoding polynucleotides. In addition, an "immunogen" is also meant to encompass any polysaccharide material useful in generating immune response. As used herein, an antigenic polypeptide or an immunogenic polypeptide is a polypeptide which, when introduced into a vertebrate, reacts with the immune system molecules of the vertebrate, i.e., is antigenic, and/or induces an immune response in the vertebrate, i.e., is immunogenic. It is quite likely that an immunogenic polypeptide will also be antigenic, but an antigenic polypeptide, because of its size or conformation, may not necessarily be immunogenic. Examples of antigenic and immunogenic polypeptides include, but are not limited to, polypeptides from infectious agents such as bacteria, viruses, parasites, or fungi, allergens such as those from pet dander, plants, dust, and other environmental sources, as well as certain self polypeptides, for example, tumor-associated antigens.

Antigenic and immunogenic polypeptides of the present invention can be used to prevent or treat, e.g., cure, ameliorate, lessen the severity of, or prevent or reduce contagion of viral, bacterial, fungal, and parasitic infectious diseases, as well as to treat allergies.

In addition, antigenic and immunogenic polypeptides of the present invention can be used to prevent or treat, e.g., cure, ameliorate, or lessen the severity of cancer including, but not limited to, cancers of oral cavity and pharynx (i.e., tongue, mouth, pharynx), digestive system (i.e., esophagus, stomach, small intestine, colon, rectum, anus, anal canal, anorectum, liver, gallbladder, pancreas), respiratory system (i.e., larynx, lung), bones, joints, soft tissues (including heart), skin, melanoma, breast, reproductive organs (i.e., cervix, endometirum, ovary, vulva, vagina, prostate, testis, penis), urinary system (i.e., urinary bladder, kidney, ureter, and other urinary organs), eye, brain, endocrine system (i.e., thyroid and other endocrine), lymphoma (i.e., hodgkin's disease, non-hodgkin's lymphoma), multiple myeloma, leukemia (i.e., acute lymphocytic leukemia, chronic lymphocytic leukemia, acute myeloid leukemia, chronic myeloid leukemia).

Examples of viral antigenic and immunogenic polypeptides include, but are not limited to, adenovirus polypeptides, alphavirus polypeptides, calicivirus polypeptides, e.g., a calicivirus capsid antigen, coronavirus polypeptides, distemper virus polypeptides, Ebola virus polypeptides, enterovirus polypeptides, flavivirus polypeptides, hepatitis virus (AE) polypeptides, e.g., a hepatitis B core or surface antigen, herpesvirus polypeptides, e.g., a herpes simplex virus or varicella zoster virus glycoprotein, immunodeficiency virus polypeptides, e.g., the human immunodeficiency virus envelope or protease, infectious peritonitis virus polypeptides, influenza virus polypeptides, e.g., an influenza A hemagglutinin, neuraminidase, or nucleoprotein, leukemia virus polypeptides, Marburg virus polypeptides, orthomyxovirus polypeptides, papilloma virus polypeptides, parainfluenza virus polypeptides, e.g., the hemagglutinin/neuraminidase, paramyxovirus polypeptides, parvovirus polypeptides, pestivirus polypeptides, picorna virus polypeptides, e.g., a poliovirus capsid polypeptide, pox virus polypeptides, e.g., a vaccinia virus polypeptide, rabies virus polypeptides, e.g., a rabies virus glycoprotein G, reovirus polypeptides, retrovirus polypeptides, and rotavirus polypeptides.

Examples of bacterial antigenic and immunogenic polypeptides include, but are not limited to, Actinomyces polypeptides, Bacillus polypeptides, Bacteroides polypeptides, Bordetella polypeptides, Bartonella polypeptides, Borrelia polypeptides, e.g., B. burgdorferi OspA, Brucella polypeptides, Campylobacter polypeptides, Capnocytophaga polypeptides, Chlamydia polypeptides, Clostridium polypeptides, Corynebacterium polypeptides, Coxiella polypeptides, Dermatophilus polypeptides, Enterococcus polypeptides, Ehrlichia polypeptides, Escherichia polypeptides, Francisella polypeptides, Fusobacterium polypeptides, Haemobartonella polypeptides, Haemophilus polypeptides, e.g., H. influenzae type b outer membrane protein, Helicobacter polypeptides, Klebsiella polypeptides, L-form bacteria polypeptides, Leptospira polypeptides, Listeria polypeptides, Mycobacteria polypeptides, Mycoplasma polypeptides, Neisseria polypeptides, Neorickettsia polypeptides, Nocardia polypeptides, Pasteurella polypeptides, Peptococcus polypeptides, Peptostreptococcus polypeptides, Pneumococcus polypeptides, Proteus polypeptides, Pseudomonas polypeptides, Rickettsia polypeptides, Rochalimaea polypeptides, Salmonella polypeptides, Shigella polypeptides, Staphylococcus polypeptides, Streptococcus polypeptides, e.g., S. pyogenes M proteins, Treponema polypeptides, and Yersinia polypeptides, e.g., Y. pestis F1 and V antigens.

Examples of fungal immunogenic and antigenic polypeptides include, but are not limited to, Absidia polypeptides, Acremonium polypeptides, Altemaria polypeptides, Aspergillus polypeptides, Basidiobolus polypeptides, Bipolaris polypeptides, Blastomyces polypeptides, Candida polypeptides, Coccidioides polypeptides, Conidiobolus polypeptides, Cryptococcus polypeptides, Curvalaria polypeptides, Epidermophyton polypeptides, Exophiala polypeptides, Geotrichum polypeptides, Histoplasma polypeptides, Madurella polypeptides, Malassezia polypeptides, Microsporum polypeptides, Moniliella polypeptides, Mortierella polypeptides, Mucor polypeptides, Paecilomyces polypeptides, Penicillium polypeptides, Phialemonium polypeptides, Phialophora polypeptides, Prototheca polypeptides, Pseudallescheria polypeptides, Pseudomicrodochium polypeptides, Pythium polypeptides, Rhinosporidium polypeptides, Rhizopus polypeptides, Scolecobasidium polypeptides, Sporothrix polypeptides, Stemphylium polypeptides, Trichophyton polypeptides, Trichosporon polypeptides, and Xylohypha polypeptides.

Examples of protozoan parasite immunogenic and antigenic polypeptides include, but are not limited to, Babesia polypeptides, Balantidium polypeptides, Besnoitia polypeptides, Cryptosporidium polypeptides, Eimeria polypeptides, Encephalitozoon polypeptides, Entamoeba polypeptides, Giardia polypeptides, Hammondia polypeptides, Hepatozoon polypeptides, Isospora polypeptides, Leishmania polypeptides, Microsporidia polypeptides, Neospora polypeptides, Nosema polypeptides, Pentatrichomonas polypeptides, Plasmodium polypeptides, e.g., P. falciparum circumsporozoite (PfCSP), sporozoite surface protein 2 (PfSSP2), carboxyl terminus of liver state antigen 1 (PfLSA1 c-term), and exported protein 1 (PfExp-1), Pneumocystis polypeptides, Sarcocystis polypeptides, Schistosoma polypeptides, Theileria polypeptides, Toxoplasma polypeptides, and Trypanosoma polypeptides.

Examples of helminth parasite immunogenic and antigenic polypeptides include, but are not limited to, Acanthocheilonema polypeptides, Aelurostrongylus polypeptides, Ancylostoma polypeptides, Angiostrongylus polypeptides, Ascaris polypeptides, Brugia polypeptides, Bunostomum polypeptides, Capillaria polypeptides, Chabertia polypeptides, Cooperia polypeptides, Crenosoma polypeptides, Dictyocaulus polypeptides, Dioctophyme polypeptides, Dipetalonema polypeptides, Diphyllobothrium polypeptides, Diplydium polypeptides, Dirofilaria polypeptides, Dracunculus polypeptides, Enterobius polypeptides, Filaroides polypeptides, Haemonchus polypeptides, Lagochilascaris polypeptides, Loa polypeptides, Mansonella polypeptides, Muellerius polypeptides, Nanophyetus polypeptides, Necator polypeptides, Nematodirus polypeptides, Oesophagostomum polypeptides, Onchocerca polypeptides, Opisthorchis polypeptides, Ostertagia polypeptides, Parafilaria polypeptides, Paragonimus polypeptides, Parascaris polypeptides, Physaloptera polypeptides, Protostrongylus polypeptides, Setaria polypeptides, Spirocerca polypeptides Spirometra polypeptides, Stephanofilaria polypeptides, Strongyloides polypeptides, Strongylus polypeptides, Thelazia polypeptides, Toxascaris polypeptides, Toxocara polypeptides, Trichinella polypeptides, Trichostrongylus polypeptides, Trichuris polypeptides, Uncinaria polypeptides, and Wuchereria polypeptides.

Examples of ectoparasite immunogenic and antigenic polypeptides include, but are not limited to, polypeptides (including protective antigens as well as allergens) from fleas; ticks, including hard ticks and soft ticks; flies, such as midges, mosquitos, sand flies, black flies, horse flies, horn flies, deer flies, tsetse flies, stable flies, myiasis-causing flies and biting gnats; ants; spiders, lice; mites; and true bugs, such as bed bugs and kissing bugs.

Examples of tumor-associated antigenic and immunogenic polypeptides include, but are not limited to, tumor-specific immunoglobulin variable regions, GM2, Tn, sTn, Thompson-Friedenreich antigen (TF), Globo H, Le(y), MUC1, MUC2, MUC3, MUC4, MUC5AC, MUC5B, MUC7, carcinoembryonic antigens, beta chain of human chorionic gonadotropin (hCG beta), HER2/neu, PSMA, EGFRvIII, KSA, PSA, PSCA, GP100, MAGE 1, MAGE 2, TRP 1, TRP 2, tyrosinase, MART-1, PAP, CEA, BAGE, MAGE, RAGE, and related proteins.

Also included as polypeptides of the present invention are antigenic or immunogenic fragments or variants of the foregoing polypeptides, and any combination of the foregoing polypeptides. Additional polypeptides may be found, for example in "Foundations in Microbiology," Talaro, et al., eds., McGraw-Hill Companies (October, 1998), Fields, et al., "Virology," 3d ed., Lippincott-Raven (1996), "Biochemistry and Molecular Biology of Parasites," Marr, et al., eds., Academic Press (1995), and Deacon, J., "Modem Mycology," Blackwell Science Inc (1997), which are incorporated herein by reference.

Preferably, the immunogen is provided by an immunogen-encoding nucleotide sequence, which, most preferably, is a plasmid DNA, or a portion thereof. The immunogenic composition can further include one or more co-lipids. These immunogenic compositions can include multiple immunogen-encoding nucleotide sequences. In addition, the immunogenic compositions of the present invention may further include one or more known immunogens including, for example, bacteria and bacterially-derived materials, viruses and virally-derived materials, poisons and venoms.

In a related aspect of the present invention is disclosed a method for inducing an immune response in a vertebrate by administering to the vertebrate an immunogenic composition, which includes one or more immunogen-encoding nucleotide sequences, and an adjuvant composition which includes one or more cationic lipid compounds according to general formula (I) or (II), in an amount sufficient to generate an immune response to the encoded immunogen. The vertebrate is preferably a mammal and, most preferably, is a human. The compositions of the present invention may also be used to enhance the humoral immune response of a vertebrate to a polynucleotide-based vaccine by administering, in addition to the nucleotide sequence, an adjuvant composition having one or more cationic lipid compounds according to general formula (I) or (II).

The immunogen-encoding nucleotide sequence (e.g., pDNA, mRNA, polynucleotide or nucleic acid oligomer) may be solubilized in any of various buffers prior to mixing or complexing with the lipid components. Suitable buffers include, for example, phosphate buffered saline (PBS), normal saline, Tris buffer, and sodium phosphate. Insoluble nucleotide sequences may be solubilized in a weak acid or weak base, and then diluted to the desired volume with a buffer. The pH of the buffer may be adjusted as appropriate. In addition, a pharmaceutically acceptable additive can be used to provide an appropriate osmolarity. Such additives are within the purview of one skilled in the art.

In preferred embodiments, nucleotide sequences are complexed with adjuvant compositions by mixing, for example, a pDNA solution and a solution of cationic lipid/co-lipid liposomes. Preferably, the concentration of each of the constituent solutions is adjusted prior to mixing such that the desired final pDNA/lipid ratio and the desired pDNA final concentration will be obtained upon mixing the two solutions. For example, if the desired final solution is to be physiological saline (0.9% weight/volume), both pDNA and liposomes are prepared in 0.9% saline and then simply mixed to afford the desired complex. The liposomes are preferably prepared by hydrating a thin film of the mixed lipid materials in an appropriate volume of aqueous solvent by vortex mixing at ambient temperatures for about one minute. The thin films are prepared by admixing chloroform solutions of the individual components to afford an equimolar solute ratio followed by aliquoting the desired volume of the solutions into a suitable container. The solvent is removed by evaporation, first with a stream of dry, inert gas (e.g., argon) followed by high vacuum treatment.

The choice of nucleotide sequence form depends in part on the desired kinetics and duration of expression. When long-term delivery of the protein encoded by the nucleotide sequence is desired, the preferred form is DNA. Alternatively, when short-term transgene protein delivery is desired, the preferred form is mRNA, since RNA is rapidly translated into pdlypeptide, but is degraded more quickly than DNA.

In one embodiment, the nucleotide sequence encoding one or more immunogens is RNA. Preferably, in this embodiment, the RNA is in the form of messenger RNA (mRNA). Methods for introducing RNA sequences into mammalian cells is described in U.S. Pat. No. 5,580,859, the disclosure of which is incorporated herein by reference. A viral alphavector, a non-infectious vector useful for administering RNA, may be used to introduce RNA into mammalian cells. Methods for the in vivo introduction of alphaviral vectors to mammalian tissues are described in Altman-Hamamdzic, S. et al., Gene Therapy 4:815–822 (1997), the disclosure of which is incorporated herein by reference.

Preferably, the immunogen-encoding nucleotide sequence is DNA. In the case of DNA, a promoter is preferably operably linked to the nucleotide sequence encoding for the immunogen. The promoter can be a cell-specific promoter that directs substantial transcription of the DNA only in predetermined cells. Other transcription control elements, besides a promoter, can be included with the nucleotide sequence to direct cell-specific transcription of the DNA. An operable linkage is a linkage in which a nucleotide sequence encoding an immunogenic molecule is connected to one or more regulatory sequences in such a way as to place expression of the immunogen under the influence or control of the regulatory sequence(s). Two DNA sequences (such as a coding sequence and a promoter region sequence linked to the 5' end of the coding sequence) are operably linked if induction of promoter function results in the transcription of mRNA encoding the desired immunogen and if the nature of the linkage between the two DNA sequences does not (1) result in the introduction of a frame-shift mutation; (2) interfere with the ability of the expression regulatory sequences to direct the expression of the immunogen; or (3) interfere with the ability of the DNA template to be transcribed. Thus, a promoter region would be operably linked to a DNA sequence if the promoter was capable of effecting transcription of that DNA sequence.

Preferably, the immunogen-encoding nucleotide sequence is part of a circular or linearized plasmid containing a non-infectious (i.e., does not infect vertebrate cells), nonintegrating (i.e., does not integrate into the genome of vertebrate cells) nucleotide sequence. A linearized plasmid is a plasmid that was previously circular but has been linearized, for example, by digestion with a restriction endonuclease. The immunogen-encoding nucleotide sequences may comprise a sequence which directs the secretion of the polypeptide.

In certain embodiments, a single immunogen-encoding nucleotide sequence encoding one or more immunogens may be administered. Alternatively, multiple immunogen-encoding nucleotide sequences each encoding one or more immunogens may be co-administered or sequentially administered. Methods of making various polynucleotide constructs comprising immunogen-encoding nucleotide sequences are disclosed in U.S. Pat. Nos. 4,713,339 and 4,965,196, the disclosures of which are incorporated herein by reference.

The present invention is also useful for delivering a biologically active agent to a cell of a plant or animal. The method involves preparing a lipid aggregate comprising the biologically active agent and a composition including one or more cationic lipid compounds according to general formula (I) or (II), followed by contacting the cell with the lipid aggregate. This method is useful for both in vivo and in vitro delivery to cells, and may be utilized for the transfection of cells.

The cationic lipid-mediated delivery of DNA and mRNA polynucleotides or proteins can provide therapy for genetic disease by supplying deficient or absent gene products to treat any genetic disease in which the defective gene or its product has been identified. Transfection may be accomplished by direct injection of cationic lipids together with DNA, RNA or proteins into cells of an vertebrate in vivo. However, cationic lipids are also effective at facilitating in vitro transfection of cells. Therefore, therapies can be alternatively carried out by in vitro transfection of some of the cells of a vertebrate using cationic lipid delivery methods, and reintroduction of the cells into the vertebrate. The ability to transfect cells at high efficiency with cationic lipids thus provides an alternate method for immunization and therapeutic treatment. The effectiveness of polynucleotide-based immunization is increased because the cytofectin compositions of the present invention also possess adjuvant characteristics.

In the practice of the present invention, administration may be performed according to any of various methods known in the art. For example, U.S. Pat. No. 5,676,954 reports on the injection of genetic material, complexed with cationic lipid carriers, into mice. Also, U.S. Pat. Nos. 5,589,466, 5,693,622, 5,580,859, 5,703,055, and PCT international patent application PCT/US94/06069 (WO 94/29469), the disclosures of which are incorporated herein by reference, provide methods for delivering DNA-cationic lipid complexes to mammals.

Specifically, the compositions of the present invention may be administered to any tissue of a vertebrate, including, but not limited to, muscle, skin, brain, lung, liver, spleen, bone marrow, thymus, heart, lymph, blood, bone, cartilage, mucosal tissue, pancreas, kidney, gall bladder, stomach, intestine, testis, ovary, uterus, vaginal tissue, rectum, nervous system, eye, gland, tongue and connective tissue. Preferably, the compositions are administered to skeletal muscle. The immunogenic compositions of the invention may also be administered to a body cavity, including, but not limited to, the lung, mouth, nasal cavity, stomach, peritoneum, intestine, heart chamber, vein, artery, capillary, lymphatic, uterus, vagina, rectum, and ocular cavity.

Preferably, the compositions of the present invention are administered by intramuscular (i.m.) or subcutaneous (s.c.) routes. Other suitable routes of administration include transdermal, intranasal, inhalation, intratracheal, transmucosal (i.e., across a mucous membrane), intra-cavity (e.g., oral, vaginal, or rectal), intraocular, vaginal, rectal, intraperitoneal, intraintestinal and intravenous (i.v.) administration.

Any mode of administration can be used so long as the administration results in desired immune response. Administration means of the present invention include, but not limited to, needle injection, catheter infusion, biolistic injectors, particle accelerators (i.e., "gene guns" or pneumatic "needleless" injectors—for example, Med-E-Jet (Vahlsing, H., et al., *J. Immunol. Methods* 171,11–22 (1994)), Pigjet (Schrijver, R., et al., *Vaccine* 15, 1908–1916 (1997)), Biojector (Davis, H., et al., *Vaccine* 12, 1503–1509 (1994); Gramzinski, R., et al., *Mol. Med.* 4, 109–118 (1998)), AdvantaJet, Medijector, gelfoam sponge depots, other commercially available depot materials (e.g., hydrojels), osmotic pumps (e.g., Alza minipumps), oral or suppositorial solid (tablet or pill) pharmaceutical formulations, topical skin creams, and decanting, use of polynucleotide coated suture (Qin et al, *Life Sciences* 65, 2193–2203 (1999)) or topical applications during surgery. The preferred modes of administration are intramuscular needle-based injection and intranasal application as an aqueous solution.

Determining an effective amount of a composition depends upon a number of factors including, for example, the chemical structure and biological activity of the substance, the age and weight of the subject, and the route of administration. The precise amount, number of doses, and timing of doses can be readily determined by those skilled in the art.

For administration to humans, the nucleotide sequence dosage in the case of immunization is preferably about 0.1–5 mg (per human subject per administration per immunogen encoded), and more preferably, is about 0.5–2.5 mg. More than one nucleotide sequence encoding different immunogens may be co-administered; thereby, the total nucleotide sequence dosage may be greater than the preferred dosage.

The present invention also provides a pharmaceutical preparation comprising a cytofectin composition including a cationic lipid compound according to general formula (I) or (II) together with a pharmacologically effective amount of a therapeutic agent, such as, for example, a therapeutic protein or polypeptide. The cytofectin composition facilitates the cellular delivery of the therapeutic agent. Preferably, the therapeutic agent is a polynucleotide, such as an antisense RNA or DNA molecule capable of encoding a molecule such as an immunogen, a natural hormone, a synthetic analogue of a naturalhormone, or a gene product that is deficient or absent in a disease state, wherein the administration of the gene product to a vertebrate has a therapeutic effect. These pharmaceutical compositions can be formulated according to known methods, whereby the substance to be delivered is combined with a pharmaceutically acceptable carrier vehicle. Suitable vehicles and their preparation are described, for example, in *Remington's Pharmaceutical Sciences*, 16$^{th}$ Edition, A. Osol, ed., Mack Publishing Co., Easton, Pa. (1980), and *Remington's Pharmaceutical Sciences*, 19$^{th}$ Edition, A. R. Gennaro, ed., Mack Publishing Co., Easton, Pa. (1995). The pharmaceutical composition can be formulated as an emulsion, gel, solution, suspension, lyophilized form, or any other form known in the art. In addition, the pharmaceutical composition can also contain pharmaceutically acceptable additives including, for example, diluents, binders, stabilizers, and preservatives.

Administration of pharmaceutically acceptable salts of the nucleotide sequence constructs described herein is preferred. Such salts can be prepared from pharmaceutically acceptable non-toxic bases including organic bases and inorganic bases. Salts derived from inorganic bases include sodium, potassium, lithium, ammonium, calcium, magnesium, and the like. Salts derived from pharmaceutically acceptable organic non-toxic bases include salts of primary, secondary, and tertiary amines, basic amino acids, and the like.

For aqueous pharmaceutical compositions used in vivo, use of sterile pyrogen-free water is preferred. Such formulations will contain an effective amount of the immunogenic composition together with a suitable amount of vehicle in order to prepare pharmaceutically acceptable compositions suitable for administration to a vertebrate.

The present invention also provides kits containing cationic lipid compounds of the invention. Such kits are useful for delivering a polypeptide to a vertebrate. Each kit includes, in the same or in a different container, a cationic lipid compound according to general formula (I) or (II) together with a co-lipid. Optionally, each kit includes a container holding 1 ng to 30 mg of a polynucleotide which operably encodes a polypeptide within vertebrate cells in vivo. Preferably, each kit includes about 100 ng to 10 mg of a polynucleobide. Any of components of the pharmaceutical kits can be provided in a single container or in multiple containers.

Any suitable container or containers may be used with pharmaceutical kits. Examples of containers include, but are not limited to, glass containers, plastic containers, or strips of plastic or paper.

Each of the pharmaceutical kits may further comprise an administration means. Means for administration include, but are not limited to syringes and needles, catheters, biolistic injectors, particle accelerators, i.e., "gene guns," pneumatic "needleless" injectors, gelfoam sponge depots, other commercially available depot materials, e.g., hydrojels, osmotic pumps, and decanting or topical applications during surgery. Each of the pharmaceutical kits may further comprise sutures, e.g., coated with the immunogenic composition (Qin et al., *Life Sciences* (1999) 65:2193–2203).

The kit can further comprise an instruction sheet for administration of the composition to a vertebrate. The polynucleotide components of the pharmaceutical composition are preferably provided as a liquid solution or they may be provided in lyophilized form as a dried powder or a cake. If the polynucleotide is provided in lyophilized form, the dried powder or cake may also include any salts, entry enhancing agents, transfection facilitating agents, and additives of the pharmaceutical composition in dried form. Such a kit may further comprise a container with an exact amount of sterile pyrogen-free water, for precise reconstitution of the lyophilized components of the pharmaceutical composition.

The container in which the pharmaceutical composition is packaged prior to use can comprise a hermetically sealed container enclosing an amount of the lyophilized formulation or a solution containing the formulation suitable for a pharmaceutically effective dose thereof, or multiples of an effective dose. The pharmaceutical composition is packaged in a sterile container, and the hermetically sealed container is designed to preserve sterility of the pharmaceutical formulation until use. Optionally, the container can be associated with administration means and/or instruction for use.

The following examples are included for purposes of illustration only and are not intended to limit the scope of the present invention, which is defined by the appended claims.

EXAMPLES

In the following examples, a quantitative comparison of the effects of the administration of various cationic lipid adjuvants with pDNA versus pDNA alone in providing anti-NP antibody responses was performed. In addition, the examples provide a quantitative comparison of transgene expression in vivo for the transfection of pDNA complexed with various cationic lipid cytofectins versus pDNA transfection alone.

Figure 2:
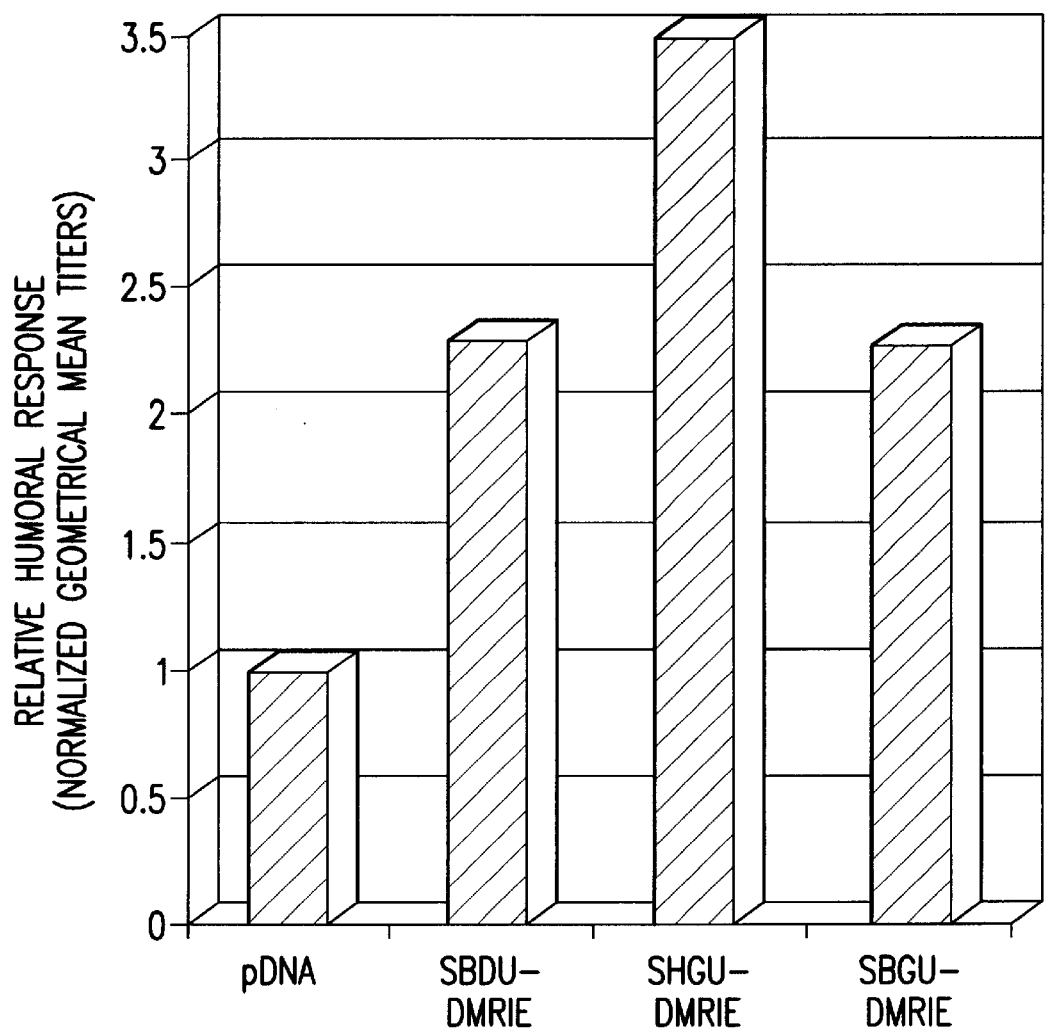
FIG. 2 is a bar graph demonstrating the enhancement of humoral immune response in mice using various adjuvant compositions comprising one of three preferred cationic lipid compounds (identified on the x-axis), as determined by antibody stimulation. The degree of enhancement provided by each adjuvant composition was evaluated using the ratio of (i) the geometric mean titer (GMT) from an adjuvant-augmented group to (ii) the GMT from pDNA administration alone, using an equivalent control group of animals (i.e., normalized GMT).
Figure 3:
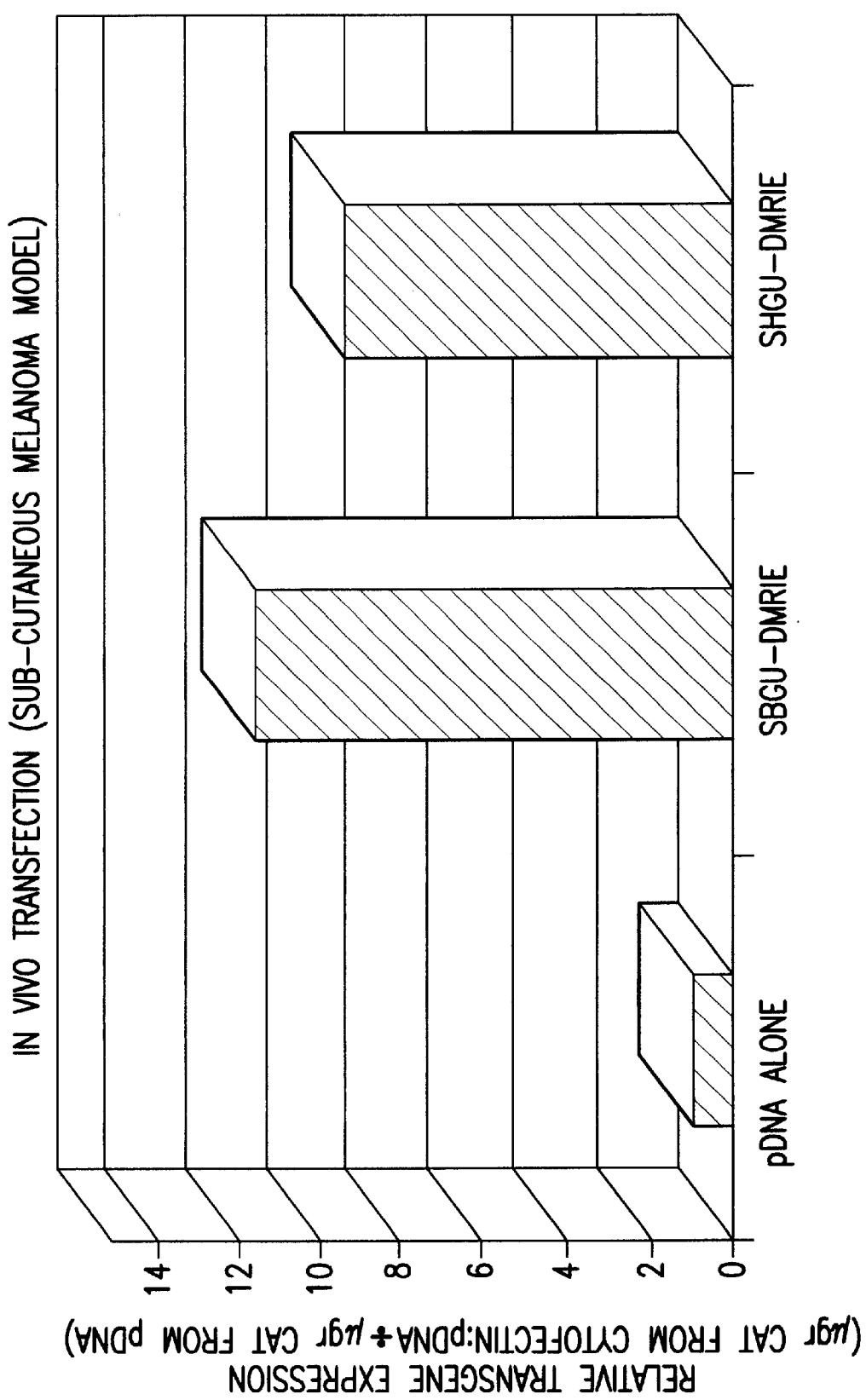
FIG. 3 is a bar graph illustrating in vivo transfection efficiency in mice using a subcutaneous melanoma model and a chloramphenicol acetyltransferase (CAT) reporter gene for two cationic lipid compounds, SBGU-DMRIE and SHGU-DMRIE (identified on the x-axis). The relative transgene expression, calculated as the ratio of μg CAT from cytofection: pDNA transfection to the μg CAT from pDNA transfection alone is shown on the y-axis.

FIG. 2 reports ratios of the geometric mean titer (GMT) from pDNA/adjuvant immunization versus the GMT from pDNA immunization alone in a murine vaccination model. Three cationic lipid compounds (SBDU-DMRIE; SHGU-DMRIE; and SBGU-DMRIE) were tested; their chemical structures are provided in FIG. 1. FIG. 3 reports the ratio of transgene expression from pDNA/cytofectin transfection to that from pDNA transfection alone for SBGU-DMRIE and SHGU-DMRIE.

Intramuscular injection of pDNA encoding for a foreign immunogen elicits both humoral and cellular immune responses. In order to determine the extent of enhancement of humoral immune response, changes in anti-NP antibody levels subsequent to immunization with an immunogen-encoding pDNA alone, and the same pDNA complexed with various cationic lipids, were quantified. The general features of the immunization assay are essentially as described by Ulmer et al. (Science 259:1745–1749 (1993)) and uses standard ELISA technology to quantify antibody titers.

Specific procedures not described in detail are either referenced or well known in the art.

Preparation of Cationic Lipid Cytofectins/Adjuvants

The general procedure for the synthesis of bis-ureyl cytofectin dimers involves coupling two copies of an alkylamino-bearing parent cytofectin by reaction with an α, ω-diisocyanate. Extractive work-up, followed by chromatographic purification, affords the desired cytofectin.

SBGU-DMRIE. GAP-DMRIE was prepared in a manner analogous to that previously published for GAP-DLRIE in Wheeler, C. J. et al., Proc Natl Acad Sci USA 93(21): 11454–11459 (1996), the disclosure of which is incorporated herein by reference. Briefly, 2,3-dimethylaminopropanediol (Aldrich) was alkylated with tetradecylmethane sulfonate (NuChekPrep) to afford the tertiary amine DMP-DMA. This amine was quatranized by treatment with 3-bromopropylphthalimide (Aldrich). Deprotection of the primary amine by phthalimide cleavage using hydrazine afforded GAP-DMRIE. Two equivalents of GAP-DMRIE were reacted with 1,4-diisocyanatobutane (Aldrich) to afford SBGU-DMRIE.

SHGU-DMRIE. Two equivalents of GAP-DMRIE were reacted with 1,6-diisocyanatohexane (Aldrich) to afford SHGU-DMRIE.

SBDU-DMRIE. DAB-DMRIE was prepared in a manner analogous to that previously published for GAP-DLRIE in Wheeler, C. J. et al., Proc Nat Acad Sci USA 93(21): 11454–11459 (1996). Briefly, 2,3-dimethylaminopropanediol (Aldrich) was alkylated with tetradecylmethane sulfonate (NuChekPrep) to afford the tertiary amine DMP-DMA. This amine was quatranized by treatment with 4-bromobutylphthalimide (Aldrich). Deprotection of the primary amine by phthalimide cleavage using hydrazine afforded DAB-DMRIE. Two equivalents of DAB-DMRIE were reacted with 1,4-diisocyanatobutane (Aldrich) to afford SBDU-DMRIE.

HB-DMRIE-Ox-Trp-γ-DMRIE. (±)-N-(3-Carboxypropyl)-N,N-dimethyl-2,3-bis(tetradecyloxy)-1-propanaminium bromide (HB-DMRIE-ox) was prepared from DMP-DMA (Wheeler et al., Biochem. Biophys. Acta-Biomembranes, 1280, 1–11 1996) by quaternization with 4-bromobutyl acetate in DMF at 100° C., followed by deprotection and oxidation of the alcohol with PDC to afford the zwitterionic lipid. To a 0° C. solution of HB-DMRIE-ox (830 mg, 1.39 mmol) in $CHCl_3$ (16 mL) was added TFA (1 eq) with stirring. After 15 min. NHS solid (240 mg, 2.09 mmol) was added followed by DCC (4.2 mL, 2.09 mmol, 0.5M in $CH_2Cl_2$). After stirring 2.5 h at 0° C., Trp-OMe HCl (354 mg, 1.39 mmol) and $Et_3N$ (0.4 mL, 2.86 mmol) in $CHCl_3$ (5 mL) were added via syringe. The mixture was left to stir overnight while warming to room temperature. The mixture was filtered, and the filtrate was washed with sat. $NaHCO_3$, dried over $Na_2SO_4$, and concentrated. The residue was chromatographed on silica gel using 85/15/0.25/0.25 $CHCl_3$/MeOH/$NH_4OH$/$H_2O$ as the eluent to afford the ester (762 mg, 60% yield). The structure and purity of the product were confirmed by $^1$H-NMR and IR.

The ester (750 mg) was hydrolyzed with 2N KOH in MeOH to afford the zwitterionic acid (610 mg, 95% yield). The acid (607 mg) was coupled with (±)-N-(3-aminopropyl)-N, N-dimethyl-2,3-bis(tetradecyloxy)-1-propanaminium bromide (GAP-DMRIE, 507 mg, prepared analogously to BAE-DMRIE in Wheeler et al., Biochem. Biophys. Acta-Biomembranes, 1280, 1–11 1996) using the procedure described above for the coupling of HB-DMRIE-ox and Trp-Ome. The title compound (170 mg) was obtained in an unoptimized 14% yield. The structure and purity of the product were confirmed by $^1$H-NMR and IR.

PentaEG-bis-DMRIE. To a stirred solution of (±)-N-(2-hydroxyethyl)-N,N-dimethyl-2,3-bis(tetradecyloxy)-1-propanaminium bromide (DMRIE, 803 mg, 1.26 mmol) prepared according to Wheeler et al., Biochem. Biophys. Acta-Biomembranes, 1280, 1–11 1996) in 1:1 THF/DMF was added NaH (151 mg, 3.78 mmol, 60% dispersion in mineral oil) in portions. After foaming subsided, solid penta(ethylene glycol) bis tosylate (345 mg, 0.62 mmol) was added in portions, and the mixture was left to stir overnight under argon. The mixture was then diluted with water, and extracted with ether twice. The combined extracts were dried over $Na_2SO_4$ and concentrated. The residue was chromatographed on silica gel using 78/20/2 $CHCl_3$/MeOH/$H_2O$ as the eluent to afford the PEGylated lipid (404 mg, 44% yield). Recrystallization could be achieved using hexane as the solvent. The structure and purity of the product were confirmed by $^1$H-NMR and IR.

PEG34-bis-But-DMRIE-propylamide. (±)-N-(3-Carboxypropyl)-N,N-dimethyl-2,3-bis(tetradecyloxy)-1-propanaminium bromide (HB-DMRIE-ox, 830 mg) was prepared and coupled as described above using poly (ethylene glycol) bis-aminopropyl terminated (n=34, 1.13 g, 0.5 eq) instead of the tryptophan methyl ester. Silica gel chromatography using 87/12/1 $CHCl_3$/MeOH/$H_2O$ as the eluent followed by trituration with hexane/ether/EtOH afforded the PEGylated lipid (452 mg, 22% yield) as a tan solid. The structure and purity of the product were confirmed by $^1$H-NMR, IR, and mass spectrometry.

Preparation of Lipid Aggregates

Cationic lipid adjuvant liposomes were prepared using the rehydrated thin-film method described above. Adjuvant/pDNA complexes were prepared by mixing equivalent volumes of a pDNA solution and a solution of cationic adjuvant liposomes.

Preparation of VR4700 (A Plasmid Encoding Influenza Nuclear Protein)

The VR4700 plasmid was prepared using standard techniques known in the art. Briefly, VR1255, an optimized plasmid encoding firefly luciferase (Hartikka, J. et al., Human Gene Therapy 7:1205–1217 (1996)), had the coding sequence for influenza nuclear protein (NP) inserted in place of the luciferase coding sequence. The influenza nuclear protein sequence was derived from a plasmid termed nCMVint-tpaPRNP (Vahlsing, L. et al., *J Immunol Methods* 174:11–22 (1994)). More specifically, the VR4700 plasmid was created via the following procedure. The VR1255 plasmid was digested with Acc I+Bam HI, then the ends were blunted with Klenow, thus affording the desired vector fragment. The nuclear protein coding sequence was obtained by digesting nCMVintTPAPRNP with Acc I+Eco RI, and blunting the ends with Klenow. Both the vector fragment and the insert fragment were purified, then ligated with T4 DNA ligase. The ligation products were transformed in *E. coli* to kanamycin resistance, after which suitable plasmid bearing clones were identified based on restriction digest profiles. Standard cell culture techniques were used to expand a suitable clone, from which the plasmid was initially isolated and purified using well known, commercially available technology (Quiagen).

Plasmid DNA was transformed into *Escherichia coli* DH10B-competent cells and grown in Terrific Broth (Sambrook, J. et al., in Molecular Cloning: A Laboratory Manual, Cold Spring Harbor Laboratory Press, Cold Spring Harbor, N.Y., p. A.2 (1989)) complemented with 50 mg/ml kanamycin in a 1 L shaker flask. Cells were harvested by centrifugation at the end of the exponential growth phase (approximately 16 hr), typically yielding 10 grams of biomass net weight per liter. Covalently closed circular pDNA was isolated by a modified lysis procedure (Horn, N. A. et al., *Human Gene Therapy* 6:565–573 (1995)) followed by standard double CsCl-ethidium bromide gradient ultracentrifugation with an average yield of approximately 5 mg per liter. Plasmids were ethanol precipitated and resolubilized in saline at 4° C. and dialyzed against saline. Endotoxin content was determined by the Limulus Amebocyte Lysate assay (Associates of Cape Cod, Inc., Falmouth, Mass.). All plasmid preparations were free of detectable RNA. Endotoxin levels were less than 0.06 Endotoxin Units/mg of plasmid DNA. The spectrophotometric $A_{260}/A_{280}$ ratios were between 1.75 and 2.0.

Animal Immunizations

Animal care throughout the study was in compliance with the "Guide for the Use and Care of Laboratory Animals," U.S. Department of Health and Human Services, National Institutes of Health (NIH Publication No. 86-23, revised 1985).

A) Murine Immunization Model. Eight to twelve-week old female BALB/c mice (Harlan Sprague Dawley, Indianapolis, Ind.) were immunized using pDNA encoding influenza nuclear protein (NP), complexed with an adjuvant at a pDNA-phosphate/adjuvant molar ratio of 4:1. Each animal in the test group (five animals per group) was injected with 50 μg pDNA in 50 μl physiological saline (0.9% NaCl weight/volume in water) per leg in the rectus femoris muscle (10 μg pDNA total per animal) alone or as a pDNA/adjuvant complex. Injections were performed at day "0" and at 3 weeks. The rectus femoris muscles of restrained, awake mice were injected using a sterile disposable, plastic insulin syringe and 28G ½ needle (Becton-Dickinson, Rutherford, N.J., Cat. No. BD9430) fitted with a plastic collar cut from a micropipette tip. The collar length was adjusted to limit the needle tip penetration to a distance of about 2 mm into the central part of the rectus femoris muscle. Injection fluids and syringes were equilibrated to room temperature and the injection of a single 50 μl volume was carried out in 1–2 seconds.

Measurement of Immune Response

A) Murine Immunization Assay. Serum was removed from the animals and the NP antibody levels were determined by serial dilution using a standard ELISA assay. Briefly, the levels of anti-NP IgG antibodies in mouse sera were determined utilizing recombinant NP protein expressed in baculovirus and used to coat ELISA plates at 0.125 mg/well. Plates were coated overnight at 4° C., washed, blocked with 5% nonfat milk, and incubated with sera for 2 hr at room temperature. After the wash, plates were incubated with alkaline phosphatase-conjugated goat anti-mouse IgG (Fc-specific, Jackson Immuno Res Labs, Bar Harbor, Me.) for 90 min at room temperature, washed again, and incubated with a substrate (p-nitrophenylphosphate) for 2 hr at room temperature. O.D. readings were taken at 405 nm using an ELISA plate reader (Molecular Devices, Menlo Park, Calif.). Titers were determined to be that serum dilution yielding an O.D. twice that for background non-immune serum.

Cationic lipid adjuvant immune response enhancement was analyzed based on the ratio of the geometric mean titer (GMT) from a adjuvant-augmented group divided by the GMT from pDNA administration alone (see FIG. 1).

Immune Response Enhancement

As shown in FIG. 2, each of the exemplified cationic lipid compounds markedly enhanced antibody responses to the encoded immunogen compared to pDNA alone.

Human Administration

Immunogenic compositions comprising pDNA encoding hemagglutinin (HA), complexed with an adjuvant (4:1 pDNA/adjuvant molar ratio), are prepared according to the method described above. Three injections of 0.1, 0.5, 1.0, or 2.5 mg pDNA in physiological saline, as a complex with the adjuvant, are injected into humans at 4-week intervals in alternate deltoids. Serum is removed from the humans and the HA antibody levels are determined by serial dilution using a standard ELISA assay, as described above. Immune responses of the human subjects to the HA antibody are induced, as indicated by normalized GMT values.

Transgene Expression Assay for In Vivo Transfection

A) General Subcutaneous Tumor Transfection Assay. Tumors are prepared by injecting a suspension of tumor cells subcutaneously on the side of a mouse strain compatible with the specific tumor type. The tumors are periodically measured. Once the tumors reach a size suitable for injection, the tumor volume is approximated based on the measured diameter assuming a spherical tumor. A complex of the cytofectin compound to be evaluated with a plasmid encoding a reporter gene (e.g., CAT) in a volume of saline equal to the volume of the tumor to be treated is then injected at a flow rate optimized for the particular tumor type. After an appropriate time, the tumors are collected, frozen and then ground up. The reporter gene product is subsequently extracted and the quantity expressed is determined using extraction and assay conditions appropriate for the particular gene product. A variety of tumor types may be evaluated using this general technique. A specific example of this assay involving melanoma tumors is provided below.

B) Subcutaneous Melanoma Tumor Model. B16F10 melanoma tumors were propagated in 90% RPMI 1640/10% Fetal Bovine Serum (FBS). The tumors were injected subcutaneously into the side of BALB/C mice in 75 μl of a suspension containing approximately $10^6$ cells/ml tissue culture medium. When the tumors reached 4.5 mm to 7.0 mm in diameter, the volume of each individual tumor was calculated by measuring the diameter of the tumor and assuming a spherical tumor. For each individual tumor, a volume of the cytofectin/CAT plasmid complex in saline equivalent to the calculated volume of the tumor was injected into the tumor at a rate of 2 ml/min. After forty-eight hours, the tumors were collected, frozen, ground up, and extracted with 1.5 ml of extraction buffer as described above. CAT activity was quantitated as described below.

Tumors were individually pulverized into a fine powder by grinding over 0.4 ml frozen lysis buffer in a 1.5 ml tube using a reversible drill and a bit that just fits into the tube, and the powder was stored in the same tube at −78° C. until extraction. Frozen powders were thawed and 100 $\mu$l Reporter Lysis Buffer from Promega (Catalog #E397A) was added to each. The samples were vortexed for fifteen minutes, frozen-thawed three times using alternating liquid nitrogen and room temperature water baths, and centrifuged three minutes at 10,000×g. The supernatant was transferred to another 1.5 ml tube and the extraction process repeated (without freeze-thawing) after adding another 500 $\mu$l lysis buffer to the pellet. The second supernatant was then combined with the first and stored at −78° C.

CAT assays were performed by the radioactive partition method of Sankaran, Anal Biochem 200:180–186 (1992) or by using a CAT ELISA kit (Boehringer Mannheim, Indianapolis, Ind.). Briefly, CAT tissue homogenates were disrupted by freeze-thawing three times in an ethanol/dry ice bath. Cellular debris was removed by centrifugation and the protein extract was incubated with $^{14}$C-chloramphenicol and acetyl CoA. The chloramphenicol was extracted with ethyl acetate and thin layer chromatography was performed to determine the $^{14}$C-chloramphenicol converted by the extracted cellular protein. Cell extracts were standardized to 2 mg protein incubated for twenty minutes. Tissue extracts were standardized to 200 mg protein incubated for four hours.

Standard curves were constructed using purified enzyme (Sigma, St. Louis, Mo.) spiked into lung extractsor enzyme provided in the ELISA kit. The two CAT assay methods yielded equivalent pg CAT per sample from the same set of extracts.

The cytofectins used were SBGU-DMRIE and SHGU-DMRIE. The results are summarized in FIG. 3, reported as averages of CAT activity. Each of the compounds exhibited greater activity than the naked DNA (pDNA) control.

Although the invention has been described with reference to the presently preferred embodiments, it should be understood that various modifications can be made without departing from the spirit of the invention. Accordingly, the invention is limited only by the following claims.

What is claimed is:

1. A cationic lipid compound of the following formula

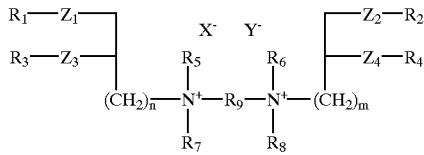

wherein $Z_1$, $Z_2$, $Z_3$ and $Z_4$ are the same or different and are —O—C(O)— or —O—;

$R_1$ and $R_2$ are the same or different and are H, $C_1$ to $C_{24}$ alkyl or $C_1$ to $C_{24}$ alkenyl;

$R_3$ and $R_4$ are the same or different and are $C_1$ to $C_{24}$ alkyl or $C_1$ to $C_{24}$ alkenyl;

$R_5$, $R_6$, $R_7$ and $R_8$ are the same or different and are H, $C_1$ to $C_{10}$ alkyl or $C_1$ to $C_{10}$ alkenyl;

$R_9$ is a linker;

n and m are the same or different and are 1 to 8; and

X and Y are the same or different and are non-toxic anions;

provided that when $R_9$ is a straight-chain alkylene having 3–6, 12, 16, 20, or 22 carbons, then all of $R_1$, $R_2$, $R_3$, and $R_4$ are not H, all of $R_5$, $R_6$, $R_7$, and $R_8$ are not methyl, m and n are not 1, and all of $Z_1$, $Z_2$, $Z_3$, and $Z_4$ are not O.

2. The compound of claim 1, wherein $R_9$ comprises $C_1$ to $C_{10}$ substituted alkyl;

$C_1$ to $C_{10}$ alkyloxy;

$C_1$ to $C_{10}$ substituted alkyloxy;

$C_1$ to $C_{10}$ alkenyl;

$C_1$ to $C_{10}$ substituted alkenyl;

$C_1$ to $C_{10}$ alkenyloxy;

$C_1$ to $C_{10}$ substituted alkenyloxy;

—NR$_{10}$—C(O)—NR$_{11}$, wherein $R_{10}$ and $R_{11}$ are independently H, $C_1$ to $C_{10}$ alkyl, $C_1$ to $C_{10}$ substituted alkyl, $C_1$ to $C_{10}$ alkenyl, or $C_1$ to $C_{10}$ substituted alkenyl;

—NR$_{12}$—C(O)—NR$_{13}$—R$_{16}$—NR$_{14}$—C(O)—NR$_{15}$, wherein $R_{12}$–$R_{15}$ are independently H, $C_1$ to $C_{10}$ alkyl, substituted $C_1$ to $C_{10}$ alkyl, $C_1$ to $C_{10}$ alkenyl, or $C_1$ to $C_{10}$ substituted alkenyl, and $R_{16}$ is independently $C_1$ to $C_{10}$ alkyl or $C_1$ to $C_{10}$ substituted alkyl;

—C(O)—NR$_{17}$, wherein $R_{17}$ is H, $C_1$ to $C_{10}$ alkyl, $C_1$ to $C_{10}$ substituted alkyl, $C_1$ to $C_{10}$ alkenyl, and $C_1$ to $C_{10}$ substituted alkenyl;

polyalkyloxy group; amino acid; peptide; saccharide; polypeptide; polysaccharide; protein; polyamine; peptidomimetic moiety; histone; moiety with DNA binding affinity; or moiety with cell receptor binding affinity.

3. The compound of claim 2, wherein $R_9$ comprises $C_1$ to $C_{10}$ substituted alkyl, $C_1$ to $C_{10}$ alkenyl or $C_1$ to $C_{10}$ substituted alkenyl.

4. The compound of claim 3, wherein $R_9$ further comprises a peptide linkage.

5. The compound of claim 4, wherein the cationic lipid compound is HB-DMRIE-Ox-Trp-$\gamma$-DMRIE.

6. The compound according to claim 1, wherein $R_9$ comprises an optionally substituted polyalkyloxy group.

7. The compound according to claim 6, wherein the polalkyloxy group contains from 1 to about 500 alkyloxy mers.

8. The compound according to claim 7, wherein the polyalkyloxy group contains from 1 to about 100 alkyloxy mers.

9. The compound according to claim 8, wherein the cationic lipid compound is PentaEG-bis-DMRIE.

10. The compound according to claim 8, wherein $R_9$ further comprises a peptide linkage.

11. The compound according to claim 10, wherein the cationic lipid compound is PEG34-bis-But-DMRIE-propylamide.

12. The compound of claim 3, wherein the linker comprises a ureyl or bis-ureyl linkage.

13. The compound of claim 1, wherein $R_9$ is a moiety with DNA binding affinity or a moiety with cell receptor binding affinity.

14. The compound of claim 13, wherein $R_9$ is an amino acid, saccharide, peptide, polysaccharide, polypeptide, protein, polyamine, or peptidomimetic moiety.

15. The compound of claim 14, wherein $R_9$ is a protein.

16. The compound of claim 15, wherein said protein is selected from the group consisting of immunoglobulins, transferrins, asialoglycoproteins, integrins, cytokines, selecting, cell surface receptors, receptor ligands, major histocompatability proteins, lysosomotrophic proteins, histones, extracellular proteins, protein hormones, growth factors, bacterial exotoxins, low density lipoprotein, alpha-2-macroglobulin, and angiotensin.

17. The compound of claim 16, wherein said protein is a transferrin.

18. The compound of claim 16, wherein said protein is an immunoglobulin.

19. The compound of claim 16, wherein said protein is a histone.

20. The compound of claim 14, wherein $R_9$ is a polyamine.

21. The compound of claim 20, wherein said polyamine is spermine, spermidine, or a derivative thereof.

22. The compound of claim 1, wherein $R_9$ comprises —$R_{17}$—$NR_{12}$—$C(O)$—$NR_{13}$-$R_{16}$—$NR_{14}$—$C(O)$—$NR_{15}$-$R_{18}$— wherein $R_{12}$-$R_{15}$ are independently H, $C_1$ to $C_{10}$ alkyl, substituted $C_1$ to $C_{10}$ alkyl, $C_1$ to $C_{10}$ alkenyl, or $C_1$ to $C_{10}$ substituted alkenyl, $R_{16}$ is independently $C_1$ to $C_{10}$ alkyl or $C_1$ to $C_{10}$ substituted alkyl, and $R_{17}$ and $R_{18}$ are independently optionally substituted $C_1$ to $C_{10}$ alkyl or $C_1$ to $C_{10}$ alkenyl.

23. The compound of claim 22, wherein the cationic lipid compound is SBDU-DMRIE, SBGU-DMRIE, or SHGU-DMRIE.

24. A composition comprising the compound of claim 1, and one or more co-lipids.

25. A composition comprising the compound of claim 5 and one or more co-lipids.

26. A composition comprising the compound of claim 9 and one or more co-lipids.

27. A composition comprising the compound of claim 11 and one or more co-lipids.

28. A composition of comprising the compound of claim 22 and one or more co-lipids.

29. A composition comprising the compound of claim 23 and one or more co-lipids.

30. An immunogenic composition comprising an immunogen and a compound of claim 1.

31. The immunogenic composition of claim 30, wherein said immunogen is an immunogen-encoding polynucleotide.

32. The immunogenic composition of claim 30 further comprising one or more co-lipids.

33. A method for inducing an immune response in a vertebrate, said method comprising administering to the vertebrate an immunogenic composition of claim 31 in an amount sufficient to generate an immune response to the encoded immunogen.

34. The method of claim 33, wherein the vertebrate is a mammal.

35. The method of claim 34, wherein the mammal is a human.

36. A method for delivering a biologically active agent to a cell of an animal, said method comprising:

contacting said cell with a lipid aggregate, said lipid aggregate comprising said biologically active agent and the compound of claim 1.

37. A pharmaceutical kit for use in delivering a polynucleotide to a vertebrate, said kit comprising:

a cationic compound of the formula

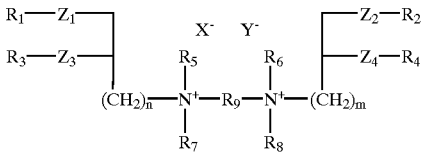

wherein $Z_1$, $Z_2$, $Z_3$ and $Z_4$ are the same or different and are —O—C(O)— or —O—;

$R_1$ and $R_2$ are the same or different and are H, $C_1$ to $C_{24}$ alkyl or $C_1$ to $C_{24}$ alkenyl;

$R_3$ and $R_4$ are the same or different and are $C_1$ to $C_{24}$ alkyl or $C_1$ to $C_{24}$ alkenyl;

$R_5$, $R_6$, $R_7$ and $R_8$ are the same or different and are H, $C_1$ to $C_{10}$ alkyl or $C_1$ to $C_{10}$ alkenyl;

$R_9$ is a linker, wherein said linker comprises $C_1$ to $C_{10}$ substituted alkyl;

$C_1$ to $C_{10}$ alkyloxy;

$C_1$ to $C_{10}$ substituted alkyloxy;

$C_1$ to $C_{10}$ alkenyl;

$C_1$ to $C_{10}$ substituted alkenyl;

$C_1$ to $C_{10}$ alkenyloxy;

$C_1$ to $C_{10}$ substituted alkenyloxy;

—$NR_{10}$—$C(O)$—$NR_{11}$, wherein $R_{10}$ and $R_{11}$ are independently H, $C_1$ to $C_{10}$ alkyl, $C_1$ to $C_{10}$ substituted alkyl, $C_1$ to $C_{10}$ alkenyl, or $C_1$ to $C_{10}$ substituted alkenyl;

—$NR_{12}$—$C(O)$—$NR_{13}$-$R_{16}$—$NR_{14}$—$C(O)$—$NR_{15}$, wherein $R_{12}$-$R_{15}$ are independently H, $C_1$ to $C_{10}$ alkyl, substituted $C_1$ to $C_{10}$ alkyl, $C_1$ to $C_{10}$ alkenyl, or $C_1$ to $C_{10}$ substituted alkenyl, and $R_{16}$ is independently $C_1$ to $C_{10}$ alkyl or $C_1$ to $C_{10}$ substituted alkyl;

—$C(O)$—$NR_{17}$, wherein $R_{17}$ is H, $C_1$ to $C_{10}$ alkyl, $C_1$ to $C_{10}$ substituted alkyl, $C_1$ to $C_{10}$ alkenyl, and $C_1$ to $C_{10}$ substituted alkenyl;

polyalkyloxy group; amino acid; peptide; saccharide; polypeptide; polysaccharide; protein; polyamine; peptidomimetic moiety; histone; moiety with DNA binding affinity; or moiety with cell receptor binding affinity.

n and m are the same or different and are 1 to 8; and

X and Y are the same or different and are non-toxic anions.;

optionally co-lipid;

optionally a polynucleotide;

one or more containers, wherein said cationic compound, said optional co-lipid, and said optional polynucleotide are in the same or different said one or more containers; and optionally means for administering to a vertebrate said cationic compound, said optional co-lipid, and said optional poylnucleotide.

38. The pharmaceutical kit according to claim 37, wherein said kit further comprises a polynucleotide, wherein said polynucleotide operably encodes a polypeptide within vertebrate cells in vivo.

39. The pharmaceutical kit according to claim 38, wherein said kit contains 1 ng to 30 mg of said polynucleotide.

40. The pharmaceutical kit according to claim 39, wherein said kit contains about 100 ng to about 10 mg of said polynucleotide.

41. The pharmaceutical kit according to claim 37, wherein $R_9$ comprises an optionally substituted polyalkyloxy group.

42. The pharmaceutical kit according to claim 41, wherein said polyalkyloxy group contains from 1 to about 500 alkyloxy mers.

43. The pharmaceutical kit according to claim 42, wherein said cationic lipid compound is PentaEG-bis-DMRIE.

44. The pharmaceutical kit according to claim 42, wherein $R_9$ further comprises a peptide linkage.

45. The pharmaceutical kit according to claim 44, wherein said cationic lipid compound is PEG34-bis-But-DMRIE-propylamide.

46. The pharmaceutical kit according to claim 37, wherein said cationic lipid compound is HB-DMRIE-Ox-Trp-γ-DMRIE.

47. The pharmaceutical kit according to claim 37, wherein $R_9$ comprises a bis-ureyl linkage.

48. The pharmaceutical kit according to claim 47, wherein said cationic lipid compound is SBDU-DMRIE, SBGU-DMRIE or SHGU-DMRIE.

49. The compound according to claim 1, wherein X and Y are Br.

50. The compound according to claim 2, where X and Y are Br.

51. The compound according to clam 22, wherein X and Y are Br.

* * * * *